United States Patent
DiMino et al.

(10) Patent No.: US 8,343,027 B1
(45) Date of Patent: Jan. 1, 2013

(54) METHODS AND DEVICES FOR PROVIDING ELECTROMAGNETIC TREATMENT IN THE PRESENCE OF A METAL-CONTAINING IMPLANT

(75) Inventors: Andre' A. DiMino, Woodcliff Lake, NJ (US); Matthew E. Drummer, Fort Lee, NJ (US); Arthur A. Pilla, Oakland, NJ (US)

(73) Assignee: Ivivi Health Sciences, LLC, San Francisco, CA (US)

( * ) Notice: Subject to any disclaimer, the term of this patent is extended or adjusted under 35 U.S.C. 154(b) by 0 days.

(21) Appl. No.: 13/361,797

(22) Filed: Jan. 30, 2012

(51) Int. Cl.
*A61N 1/00* (2006.01)
(52) U.S. Cl. ................. 600/13; 600/14; 607/52
(58) Field of Classification Search ............ 600/9–15; 607/1, 2, 45, 46, 48, 50–52, 65–67, 72–74, 607/76, 115, 152
See application file for complete search history.

(56) References Cited

U.S. PATENT DOCUMENTS

| | | | |
|---|---|---|---|
| 1,233,841 | A | 7/1917 | Butcher |
| 2,130,758 | A | 9/1938 | Rose |
| 2,276,996 | A | 3/1942 | Milinowski |
| 2,648,727 | A | 8/1953 | Rockwell |
| 3,043,310 | A | 7/1962 | Milinowski |
| 3,181,535 | A | 5/1965 | Milinowski |
| 3,270,746 | A | 9/1966 | Kendall et al. |
| 3,329,148 | A | 7/1967 | Kendall |
| 3,329,149 | A | 7/1967 | Kendall et al. |
| 3,800,802 | A | 4/1974 | Berry et al. |
| 3,890,953 | A | 6/1975 | Kraus et al. |
| 3,952,751 | A | 4/1976 | Yarger |
| 3,978,864 | A | 9/1976 | Smith |
| 4,028,518 | A | 6/1977 | Boudouris et al. |
| 4,105,017 | A | 8/1978 | Ryaby et al. |
| 4,197,851 | A | 4/1980 | Fellus |
| 4,266,532 | A | 5/1981 | Ryaby et al. |
| 4,305,115 | A | 12/1981 | Armitage |
| 4,315,503 | A | 2/1982 | Ryaby et al. |
| 4,338,945 | A | 7/1982 | Kosugi et al. |
| 4,374,482 | A | 2/1983 | Moore et al. |
| 4,454,882 | A | 6/1984 | Takano |
| 4,616,629 | A | 10/1986 | Moore |

(Continued)

FOREIGN PATENT DOCUMENTS

CA 0608693 11/1960

(Continued)

OTHER PUBLICATIONS

Pilla et al.; U.S. Appl. No. 13/252,114 entitled "Method and apparatus for electromagnetic treatment of head, cerebral and neural injury in animals and humans," filed Oct. 2, 2011.

(Continued)

*Primary Examiner* — Charles A Marmor, II
*Assistant Examiner* — Carrie R Dorna
(74) *Attorney, Agent, or Firm* — Shay Glenn LLP

(57) ABSTRACT

Methods and devices for providing electromagnetic field treatment to a subject having a metal-containing implant or prosthesis at or near the treatment site. These treatment methods can include calibrating the treatment devices such that the treatment field provided is not distorted or affected by the presence of metal in the target location. Additionally, embodiments of the invention provide for wearable and adjustable electromagnetic treatment devices with reinforcing support members to maintain the structure of flexible metal applicators, which generate the therapeutic electromagnetic field.

11 Claims, 31 Drawing Sheets

U.S. PATENT DOCUMENTS

| | | | |
|---|---|---|---|
| 4,627,438 A | 12/1986 | Liss et al. |
| 4,654,574 A | 3/1987 | Thaler |
| 4,672,951 A | 6/1987 | Welch |
| 4,674,482 A | 6/1987 | Waltonen et al. |
| 4,793,325 A | 12/1988 | Cadossi et al. |
| 4,829,984 A | 5/1989 | Gordon |
| 4,889,526 A | 12/1989 | Rauscher et al. |
| 4,926,881 A | 5/1990 | Ichinomiya et al. |
| 4,993,413 A | 2/1991 | McLeod et al. |
| 4,998,532 A | 3/1991 | Griffith |
| 5,000,178 A | 3/1991 | Griffith |
| 5,014,699 A | 5/1991 | Pollack et al. |
| 5,123,898 A | 6/1992 | Liboff et al. |
| 5,181,902 A | 1/1993 | Erickson et al. |
| 5,224,922 A | 7/1993 | Kurtz |
| 5,338,286 A | 8/1994 | Abbott et al. |
| 5,370,680 A | 12/1994 | Proctor |
| 5,386,837 A | 2/1995 | Sterzer |
| 5,407,421 A | 4/1995 | Goldsmith |
| 5,478,303 A | 12/1995 | Foley-Nolan et al. |
| 5,480,373 A | 1/1996 | Fischer et al. |
| 5,518,496 A | 5/1996 | McLeod et al. |
| 5,584,863 A | 12/1996 | Rauch et al. |
| 5,718,246 A | 2/1998 | Vona |
| 5,718,721 A | 2/1998 | Ross |
| 5,723,001 A | 3/1998 | Pilla et al. |
| 5,743,844 A | 4/1998 | Tepper et al. |
| 5,778,894 A | 7/1998 | Dorogi et al. |
| 5,792,209 A | 8/1998 | Varner et al. |
| 5,814,078 A | 9/1998 | Zhou et al. |
| 5,877,627 A | 3/1999 | Fischer et al. |
| 5,908,444 A | 6/1999 | Azure |
| 5,951,459 A | 9/1999 | Blackwell |
| 5,968,527 A | 10/1999 | Litovitz |
| 5,990,177 A | 11/1999 | Brown |
| 5,997,464 A | 12/1999 | Blackwell |
| 6,004,257 A | 12/1999 | Jacobson |
| 6,083,149 A | 7/2000 | Wascher et al. |
| 6,086,525 A | 7/2000 | Davey et al. |
| 6,099,459 A | 8/2000 | Jacobson |
| 6,132,362 A | 10/2000 | Tepper et al. |
| 6,149,577 A | 11/2000 | Bouldin et al. |
| 6,155,966 A | 12/2000 | Parker |
| 6,190,893 B1 | 2/2001 | Shastri et al. |
| 6,200,259 B1 | 3/2001 | March |
| 6,213,934 B1 | 4/2001 | Bianco et al. |
| 6,231,528 B1 | 5/2001 | Kaufman et al. |
| 6,234,953 B1 | 5/2001 | Thomas et al. |
| 6,246,912 B1 | 6/2001 | Sluijter et al. |
| 6,261,221 B1 | 7/2001 | Tepper et al. |
| 6,261,831 B1 | 7/2001 | Agee |
| 6,301,506 B1 | 10/2001 | den Boer et al. |
| 6,321,120 B1 | 11/2001 | Surbeck et al. |
| 6,334,069 B1 | 12/2001 | George et al. |
| 6,418,345 B1 | 7/2002 | Tepper et al. |
| 6,421,562 B1 | 7/2002 | Ross |
| 6,424,863 B1 | 7/2002 | Flock et al. |
| 6,434,426 B1 | 8/2002 | Munneke et al. |
| 6,443,883 B1 | 9/2002 | Ostrow et al. |
| 6,458,151 B1 | 10/2002 | Saltiel |
| 6,458,157 B1 | 10/2002 | Suaning et al. |
| 6,463,336 B1 | 10/2002 | Mawhinney |
| 6,556,872 B2 | 4/2003 | Hauck |
| 6,560,489 B2 | 5/2003 | Hauck |
| 6,561,968 B1 | 5/2003 | Dissing et al. |
| 6,569,654 B2 | 5/2003 | Shastri et al. |
| 6,589,159 B2 | 7/2003 | Paturu |
| 6,629,971 B2 | 10/2003 | McDaniel |
| 6,648,812 B2 | 11/2003 | Ardizzone |
| 6,675,047 B1 | 1/2004 | Konoplev et al. |
| 6,678,562 B1 | 1/2004 | Tepper et al. |
| 6,684,108 B1 | 1/2004 | Surbeck et al. |
| 6,701,185 B2 | 3/2004 | Burnett et al. |
| 6,839,589 B2 | 1/2005 | Petlan |
| 6,844,378 B1 | 1/2005 | Martin et al. |
| 6,919,205 B2 | 7/2005 | Brighton |
| 6,934,580 B1 | 8/2005 | Osorio et al. |
| 6,955,642 B1 | 10/2005 | Simon |
| 7,010,353 B2 | 3/2006 | Gan et al. |
| 7,022,506 B2 | 4/2006 | Brighton et al. |
| 7,089,060 B1 | 8/2006 | Fitzsimmons |
| 7,130,692 B2 | 10/2006 | Brighton et al. |
| 7,160,241 B1 | 1/2007 | Herbst |
| 7,175,587 B2 | 2/2007 | Gordon et al. |
| 7,177,695 B2 | 2/2007 | Moran |
| 7,177,696 B1 | 2/2007 | Pandelisev |
| 7,215,995 B2 | 5/2007 | Brighton et al. |
| 7,288,062 B2 | 10/2007 | Spiegel |
| 7,333,858 B2 | 2/2008 | Killian et al. |
| 7,419,474 B2 | 9/2008 | Lee |
| 7,429,471 B2 | 9/2008 | Brighton |
| 7,456,189 B2 | 11/2008 | Himmelsbach et al. |
| 7,465,546 B2 | 12/2008 | Brighton |
| 7,465,566 B2 | 12/2008 | Brighton et al. |
| 7,520,849 B1 | 4/2009 | Simon |
| 7,566,295 B2 | 7/2009 | Giardino et al. |
| 7,740,574 B2 | 6/2010 | Pilla et al. |
| 7,744,524 B2 | 6/2010 | Pilla |
| 7,758,490 B2 | 7/2010 | Pilla et al. |
| 7,896,797 B2 | 3/2011 | Pilla et al. |
| 2001/0007937 A1 | 7/2001 | MacKin |
| 2001/0031906 A1 | 10/2001 | Ishikawa et al. |
| 2001/0044643 A1 | 11/2001 | Litovitz |
| 2002/0035358 A1 | 3/2002 | Wang |
| 2003/0023283 A1 | 1/2003 | McDaniel |
| 2003/0028072 A1 | 2/2003 | Fischell et al. |
| 2003/0093028 A1 | 5/2003 | Spiegel |
| 2003/0099979 A1 | 5/2003 | Ohtani et al. |
| 2003/0125769 A1 | 7/2003 | Brighton |
| 2003/0171640 A1 | 9/2003 | Canedo |
| 2004/0176803 A1 | 9/2004 | Whelan et al. |
| 2004/0176805 A1 | 9/2004 | Whelan et al. |
| 2004/0176806 A1 | 9/2004 | Markoll |
| 2004/0267333 A1 | 12/2004 | Kronberg |
| 2005/0049640 A1 | 3/2005 | Gurtner et al. |
| 2005/0059153 A1 | 3/2005 | George et al. |
| 2005/0215842 A1 | 9/2005 | Pilla et al. |
| 2005/0222625 A1 | 10/2005 | Laniado et al. |
| 2005/0251229 A1 | 11/2005 | Pilla et al. |
| 2005/0288744 A1* | 12/2005 | Pilla et al. ................ 607/86 |
| 2006/0009825 A1 | 1/2006 | Chiriaev et al. |
| 2006/0161226 A1 | 7/2006 | McMickle |
| 2006/0206174 A1 | 9/2006 | Honeycutt et al. |
| 2006/0212077 A1 | 9/2006 | Pilla et al. |
| 2006/0293724 A1 | 12/2006 | Kronberg et al. |
| 2007/0026514 A1 | 2/2007 | Pilla et al. |
| 2007/0149901 A1 | 6/2007 | Gordon et al. |
| 2007/0173904 A1 | 7/2007 | Pilla |
| 2007/0282156 A1 | 12/2007 | Konings |
| 2007/0288072 A1 | 12/2007 | Pascual-Leone et al. |
| 2007/0299472 A1 | 12/2007 | Brighton |
| 2008/0039901 A1 | 2/2008 | Kronberg et al. |
| 2008/0058793 A1 | 3/2008 | Pilla et al. |
| 2008/0132971 A1 | 6/2008 | Pille et al. |
| 2008/0140155 A1 | 6/2008 | Pilla et al. |
| 2008/0200749 A1 | 8/2008 | Zheng et al. |
| 2008/0217263 A1 | 9/2008 | Higgins et al. |
| 2008/0288035 A1 | 11/2008 | Gill et al. |
| 2009/0018613 A1 | 1/2009 | Brighton |
| 2009/0030476 A1 | 1/2009 | Hargrove |
| 2009/0043188 A1 | 2/2009 | Rauscher |
| 2009/0105781 A1 | 4/2009 | Brighton |
| 2009/0216068 A1 | 8/2009 | Thomas et al. |
| 2010/0179373 A1 | 7/2010 | Pille et al. |
| 2010/0210893 A1 | 8/2010 | Pilla |
| 2010/0222631 A1 | 9/2010 | Pilla |
| 2011/0112352 A1 | 5/2011 | Pilla et al. |
| 2011/0152598 A1 | 6/2011 | Pilla et al. |
| 2011/0207989 A1 | 8/2011 | Pilla et al. |

FOREIGN PATENT DOCUMENTS

| | | |
|---|---|---|
| CN | 1052053 A | 6/1991 |
| DE | 970276 | 9/1958 |
| EP | 543152 A2 | 10/1992 |
| EP | 0500983 | 7/1995 |
| FR | 748828 | 4/1933 |
| GB | 0604107 | 6/1948 |

| | | |
|---|---|---|
| GB | 2162066 | 1/1986 |
| GB | 2400316 A | 10/2004 |
| JP | 03-523271 | 8/2003 |
| WO | WO 83/01742 A1 | 5/1983 |
| WO | WO 95/27533 | 10/1995 |
| WO | WO 96/11723 | 4/1996 |
| WO | WO 2004/108208 A2 | 12/2004 |
| WO | WO 2009/155516 | 12/2009 |

OTHER PUBLICATIONS

Pilla, Arthur A.; U.S. Appl. No. 13/285,761 entitled "Method and apparatus for electromagnetic enhancement of biochemical signaling pathways for therapeutics and prophylaxis in plants, animals and humans," filed Oct. 31, 2011.

Aaron et al.; Power frequency fields promote cell differentiation coincident with an increase in transforming growth factor-?1 expression; bioelectromagnetics; vol. 20; pp. 453-458; 1999.

Aaron et al.; The conservative treatment of osteonecrosis of the femoral head. A comparison of core decompression and pulsing electromagnetic fields; Clin. Orthopaed. Rel. Res.; vol. 249; pp. 209-218; 1989.

Adair; A physical analysis of the ion parametric resonance model; Bioelectromagnetics; vol. 19; pp. 181-191; 1998.

Adair; Comment: Analyses of Models of Ion Actions Under the Combined Action of AC and DC Magnetic Fields; Bioelectromagnetics; vol. 27; No. 4; pp. 332-334; 2006.

Adair; Criticism of Lednev's mechanism for the influence of weak magnetic fields on biological systems; Bioelectromagnetics; vol. 13; pp. 231-235; 1992.

Adair; Static and low-frequency magnetic field effects: Health risks and therapies; Rep Prog Phys; vol. 63; pp. 415-454; 2000.

Akai et al.; Effect of electrical stimulation on musculoskeletal systems: a meta-analysis of controlled clinical trials; Bioelectromagnetics; vol. 23; pp. 132-143; 2002.

Ayrapetyan et al.; Magnetic fields alter electrical properties of solutions and their physiological effects; Bioelectromagnetics; vol. 15; pp. 133-142; 1994.

Bassett et al.; A non-operative salvage of surgically-resistant pseudoarthroses and non-unions by pulsing electromagnetic fields; Clin Orthop; vol. 124; pp. 117-131; 1977.

Bawin et al.; Effects of modulated VHF fields on the central nervous system; Ann NYAcad Sci; vol. 247; pp. 74-81; 1975.

Bawin et al.; Sensitivity of calcium binding in cerebral tissue to weak environmental electric fields oscillating at low frequency; Proc Nat'l Acad Sci, USA; pp. 1999-2003; 1976.

Bearden Jr.; Quantitation of submicrogram quantities of protein by an improved protein-dye binding assay; Biochim Biophys Acta; vol. 533; pp. 525-529; 1978.

Belyaev et al.; Frequency-dependent Effects of ELF Magnetic Field on Cromatin Conformation in *Escherichia coli* Cells and Human Lymphocytes; Biochimica et Biophysica Acta; vol. 1526; pp. 269-276; 2001.

Binder et al.; Pulsed electromagnetic field therapy of persistent rotator cuff tendinitis: a double blind controlled assessment; Lancet; vol. 1 (8379); pp. 695-697; 1984.

Blackman et al.; A role for the magnetic field in the radiation induced efflux of calcium ions from brain tissue in vitro; Bioelectromagnetics; vol. 6; pp. 327-337; 1985.

Blackman et al.; Empirical test of an ion parametric resonance model for magnetic field interactions with PC-12 cells; Bioelectromagnetics; vol. 15: pp. 239-260; 1994.

Blackman et al.; Influence of electromagnetic fields on the efflux of calcium ions from brain tissue in vitro: A three-model analysis consistent with the frequency response up to 510 Hz; Bioelectromagnetics; vol. 9; pp. 215-227; 1988.

Blackman et al.; Multiple power-density windows and their possible origin; Bioelectromagnetics; vol. 10; pp. 115-128; 1989.

Blanchard et al.; Clarification and application of an ion parametric resonance model for magnetic field interactions with biological systems; Bioelectromagnetics; vol. 15; pp. 217-238; 1994.

Blank et al.; Do electromagnetic fields interact directly with DNA?; Bioelectromagnetics; vol. 18; pp. 111-115; 1997.

Blumenthal et al.; Effects of low-intensity AC and/or DC electromagnetic fields on cell attachment and induction of apoptosis; Bioelectromagnetics; vol. 18; pp. 264-272; 1997.

Cain; Stimulating Treatment; Orthopedic Technology Review; vol. 4; No. 4; pp. 31-34; 2002.

Chiabrera et al.; Effect of Lifetimes on Ligand Binding Modelled by the Density Operator; Bioelectrochemistry and Bioenergetics; vol. 30; pp. 35-42; 1993.

Clapham, D.; Calcium signaling; Cell; vol. 80; pp. 259-268; 1995.

Colbert et al.; Magnetic mattress pad use in patients with fibromyalgia: A randomized double-blind pilot study; J Back Musculoskeletal Rehab; vol. 13; 19-31; 1999.

Collacott et al.; Bipolar permanent magnets for the treatment of low back pain: A pilot study; JAMA; vol. 283; No. 10; pp. 1322-1325; Mar. 8, 2000.

Cox, J.; Interactive Properties of Calmodulin; Biochem J.; vol. 249; pp. 621-629; 1988.

Edmonds, D.; Larmor precession as a mechanism for the detection of static and alternating magnetic fields; Bioelectrochemistry and Bioenergetics; vol. 30; pp. 3-12; 1993.

Engström, S.; Dynamic properties of Lednev's parametric resonance mechanism; Bioelectromagnetics; vol. 17; pp. 58-70; 1996.

Fitzsimmons et al.; Combined magnetic fields increase net calcium flux in bone cells. Calcif. Tiss. Intl.; vol. 55; pp. 376-380; 1994.

Halle, B.; On the cyclotron resonance mechanism for magnetic field effects on transmembrane ion conductivity; bioelectromagnetics; vol. 9; pp. 381-385; 1988.

Johansson, et al.; Brij 58, a polyoxyethylene acyl ether, creates membrane vesicles of uniform sidedness: A new tool to obtain inside-out (cytoplasmic side-out) plasma membrane vesicle; Plant J.; vol. 7; pp. 165-173; 1995.

Kloth et al.; Effect of Pulsed Radio Frequency Stimulation on Wound Healing: A Double-Blind Pilot Clinical Study; in "Electricity and Magnetism in Biology and Medicine"; Bersani F, ed Plenum, New York; pp. 875-878; 1999.

Koch, et al.; Interaction between weak low-frequency magnetic fields and cell membranes; Bioelectromagnetics; vol. 24; pp. 39-402; 2003.

Körner et al.; Surface properties of right side-out plasma membrane vesicles isolated from barley roots and leaves; Plant Physiol.; vol. 79; pp. 72-79; 1985.

Lansdown et al.; Sequential changes in trace metal, metallothionein and calmodulin concentrations in healing skin wounds; J. Anat.; vol. 195; pp. 375-386; 1999.

Larsson et al.; Isolation of highly purified plant plasma membranes and separation of inside-out and rightside-out vesicles; Methods Enzymol; vol. 228; pp. 451-469; 1994.

Liboff, et al.; Geomagnetic cyclotron resonance in living cells; J Biol Phys; vol. 9; pp. 99-102; 1985.

Liboff, et al.; Kinetics of channelized membrane ions in magnetic fields; Bioelectromagnetics; vol. 9; pp. 39-51; 1988.

Likic et al.; Dynamics of Ca2+saturated Calmodulin D129N Mutant Studied by Multiple Molecular Dynamics Simulations; Protein Sci; vol. 12; pp. 2215-2229; 2003.

Lukas, T.; A Signal Transduction Pathway Model Prototype II: Application to Ca21-Calmodulin Signaling and Myosin Light Chain Phosphorylatiori; Biophysical Journal; vol. 87; pp. 1417-1425; 2004.

Man, et al.; The influence of permanent magnetic field therapy on wound healing in suction lipectomy patients: A double-blind study; Plastic and Reconstructive Surgery; vol. 104; pp. 2261-2296; 1999 (printed Jul. 17, 2010).

Markov, et al.; Weak static magnetic field modulation of myosin phosphorylation in a cell-free preparation: Calcium dependence; Bioelectrochemistry and Bioenergetics; vol. 43; pp. 233,238; 1997.

McDonald, F.; Effect of static magnetic fields on osteoblasts and fibroblasts in-vitro; Bioelectromagnetics; vol. 14; pp. 187-196; 1993.

McLean, et al.; Blockade of sensory neuron action potentials by a static magnetic field in the 10 mT range; Bioelectromagnetics; vol. 16; pp. 20-32; 1995.

McLeod, et al.; Dynamic characteristics of membrane ions in multifield configurations of low-frequency electromagnetic radiation; Bioelectromagnetics; vol. 7; pp. 177-189; 1986.

Mehler, et al.; Structural Dynamics of Calmodulin and Troponin C; Protein Engineering; vol. 4; No. 6; pp. 625-627; 1991.

Mooney; A randomized double blind prospective study of the efficacy of pulsed electromagnetic fields for interbody lumbar fusions; Spine; vol. 15; pp. 708-715; 1990.

Muehsam et al.; Lorentz Approach to Static Magnetic Field Effects on Bound Ion Dynamics and Binding Kinetics: Thermal Noise Considerations; Bioelectromagnetics; vol. 17; pp. 89-99; 1996.

Muehsam et al.; Weak Magnetic Field Modulation of Ion Dynamics in a Potential Well: Mechanistic and Thermal Noise Considerations; Bioelectrochem Bioenergetics; vol. 28; pp. 355-365; 1994.

Muehsam, et al.; The sensitivity of cells and tissues to exogenous fields: effects of target system initial state; Bioelectrochemistry and Bioenergetics; vol. 48; pp. 35-42; 1999.

Pilla et al.; EMF signals and ion/ligand binding kinetics:prediction of bioeffective waveform parameters; Bioelectrochemistry and Bioenergetics; vol. 48; pp. 27-34; 1999.

Pilla; Electrochemical information transfer at living cell membrane; Ann. N.Y.Acad. Sci.; vol. 238; p. 149-170; 1974.

Pilla; Low-intensity electromagnetic and mechanical modulation of bone growth and repair are they equivalent?; Journal of Orthopedic Science; vol. 7; pp. 420-428; 2002.

Pilla; State of the art in electromagnetic therapeutics: soft tissue applications; Electricity and Magnetism in Biology and Medicine; Bersani (ed.); Kluwer Academic/Plenum Publishers; pp. 871-874; 1999.

Pilla; Weak time-varying and static magnetic fields: from Mechanisms to therapeutic applications; Biological Effects of Electro Magnetic Fields; P. Stavroulakis, ed. Springer Verlag; pp. 34-75; 2003.

Ryaby et al.; The role of insulin-like growth factor in magnetic field regulation of bone formation. Bioelectrochem. Bioenergetics; vol. 35; pp. 87-91; 1994.

Sisken, et al.; Static magnetic fields and nerve regeneration (presentation abstract); Bioelectromagnetics Society; 21st Ann Meeting, Long Beach, Jun. 20-24, 1999.

Valbona, et al.; Response of pain to static magnetic fields in post-polio patients: A doubleblind pilot study; Arch. Phys. Med. Rehabil.; vol. 78; pp. 1200-1203; 1997.

Weaver, et al.; The response of living cells to very weak electric fields: The thermal noise limit; Science; vol. 247; pp. 459-462; 1990.

Zhadin, M.; Combined action of static and alternating magnetic fields on ion motion in a macromolecule; Theoretical aspects; Bioelectromagnetics; vol. 19; pp. 279-292; 1998.

Zhuang et al.; Electrical stimulation induces the level of TGF-B 1 mRNA in osteoblastic cells by amechanism involving calcium/calmodulin pathway; Biochem. Biophys. Res. Comm.; vol. 237;pp. 225-229; 1997.

Zdeblick; A prospective, randomized study of lumbar fusion: preliminary results; Spine; vol. 18; pp. 983-991; 1993.

Albensi et al.; Diffusion and high resolution MRI of traumatic brain injury in rats: time course and correlation with histology. Exp Neurol 162, 61-72 (Mar. 2000).

Anderson et al.; Fluoro-jade B stains quiescent and reactive astrocytes in the rodent spinal cord. J Neurotrauma 20, 1223-31 (Nov. 2003).

Armonda et al.; Wartime traumatic cerebral vasospasm: recent review of combat casualties. Neurosurgery 59, 1215-25; discussion 1225 (Dec. 2006).

Arnold et al.; Nitric oxide activates guanylate cyclase and increases guanosine 3':5'-cyclic monophosphate levels in various tissue preparations. Proc Natl Acad Sci U S A 74, 3203-7 (Aug. 1977).

Auffray et al.; Blood monocytes: development, heterogeneity, and relationship with dendritic cells. Annu Rev Immunol 27, 669-92 (Jan. 2009).

Bassett et al.; Generation of electric potentials by bone in response to mechanical stress. Science 137, 1063-4 (Sep. 28, 1962).

Bassett, C. A.; Biological significance of piezoelectricity. Calc. Tiss. Res. 1, 252 (Dec. 1968).

Beaumont et al.; The effects of human corticotrophin releasing factor on motor and cognitive deficits after impact acceleration injury. Neurol Res 22, 665-73 (Oct. 2000).

Beaumont et al.; The impact-acceleration model of head injury: injury severity predicts motor and cognitive performance after trauma. Neurol Res 21, 742-54, (Dec. 2009).

Beck et al.; The Bioelectromagnetics Society (History of the first 25 years); eds. Shappard, A. and Blackman, C.; 46 pgs.; (mo. unavailable) 2004.

Becker, T. O.; The bioelectric factors in amphibian limb regeneration. J. Bone Joint Surg. 43A, 643 (Jul. 1961).

Bederson et al.; Nuclear magnetic resonance imaging and spectroscopy in experimental brain edema in a rat model. J Neurosurg 64, 795-802 (May 1986).

Belanger et al.; Cognitive sequelae of blast-related versus other mechanisms of brain trauma. J Int Neuropsychol Soc 15(1), Jan. 1-8, 2009.

Blackman et al.; Action of 50 Hz magnetic fields on neurite outgrowth in pheochromocytoma cells. Bioelectromagnetics 14, 273-86 (mo. unavailable) (1993).

Blackman et al.; Effects of ELF fields on calcium-ion efflux from brain tissue, in vitro; Radiat Res; vol. 92(3); pp. 510-520; Dec. 1982.

Borbely et al.; Pulsed high-frequency electromagnetic field affects human sleep and sleep electroencephalogram. Neurosci Lett 275, 207-10 (Nov. 19, 1999).

Bracken et al.; Administration of methylprednisolone for 24 or 48 hours or tirilazad mesylate for 48 hours in the treatment of acute spinal cord injury. Results of the Third National Acute Spinal Cord Injury Randomized Controlled Trial. National Acute Spinal Cord Injury Study. Jama 277, 1597-604 (May 28, 1997).

Bredt, D. S.; Nitric oxide signaling specificity-the heart of the problem. J Cell Sci 116, Jan. 9-15, 2003.

Brighton et al.; Signal transduction in electrically stimulated bone cells. J Bone Joint Surg Am 83-A, 1514-23 (Oct. 2001).

Brighton, C. T.; The treatment of non-unions with electricity. J Bone Joint Surg Am 63, 847-51 (Jun. 1981).

Brooks et al.; Magnetic resonance spectroscopy in traumatic brain injury. J Head Trauma Rehabil 16, 149-64 (Apr. 2001).

Burton, T.; New Test for Brain Injury on Horizon, The Wall Street Journal, New York, (Jul. 20, 2010).

Cammermeyer, J.; I. An evaluation of the significance of the "dark" neuron. Ergeb Anat Entwicklungsgesch 36, 1-61 (mo. unavailable) (1962).

Canals et al.; Neurotrophic and neurotoxic effects of nitric oxide on fetal midbrain cultures. J Neurochem 76, 56-68 (Jan. 2001).

Canseven et al.; Effects of ambient ELF magnetic fields: variations in electrolyte levels in the brain and blood plasma; Gazi Tip Dergisi / Gazi Medical Journal; 16(3); pp. 121-127; Sep. 2005.

Casper et al.; Dopaminergic neurons associate with blood vessels in neural transplants. Exp Neurol 184, 785-93 (Dec. 2003).

Casper et al.; Enhanced vascularization and survival of neural transplants with ex vivo angiogenic gene transfer. Cell Transpl. 11, 331-349 (mo. unavailable) (2002).

Cederberg et al.; What has inflammation to do with traumatic brain injury? Childs Nery Syst 26, 221-6 (Feb. 2010).

Cernak et al.; Cognitive deficits following blast injury-induced neurotrauma: possible involvement of nitric oxide. Brain lnj 15, 593-612 (Jul. 2001).

Cernak et al.; Traumatic brain injury: An overview of pathobiology with emphasis on military populations. J Cereb Blood Flow Metab 30, 255-66 (Feb. 2010).

Cernak et al.; Ultrastructural and functional characteristics of blast injury-induced neurotrauma. J Trauma 50, 695-706 (Apr. 2001).

Chiabrera et al.; Bioelectromagnetic Resonance Interactions: Endogenous Field and Noise. In "Interaction Mechanisms of Low-Level Electromagnetic Fields in Living Systems." Oxford University Press. 164.179; Dec. 1992.

Chiabrera et al.; Quantum dynamics of ions in molecular crevices under electromagnetic exposure; (Brighton C, Pollak S, editors); Electromagnetics in biology and medicine; San Francisco, USA; San Francisco Press; pp. 21-26; Jun. 1991.

Chiabrera et al.; The role of the magnetic field in the EM interaction with ligand binding; In: "Mechanistic Approaches to Interaction of Electric and Electromagnetic Fields With Living Systems;" Blank, Findl (eds); New York; Plenum Press; pp. 79-95; Oct. 31, 1987.

Ciani et al.; Akt pathway mediates a cGMP-dependent survival role of nitric oxide in cerebellar granule neurones. J Neurochem 81, 218-28 (Apr. 2002).

Colomer et al.; Physiological roles of the Ca2+/CaM-dependent protein kinase cascade in health and disease. Subcell Biochem 45, 169-214 (mo. unavailable) (2007).

Cook et al.; Resting EEG is affected by exposure to a pulsed ELF magnetic field. Bioelectromagnetics 25, 196-203 (Apr. 2004).

Cook et al.; The effects of pulsed, high-frequency radio waves on the rate of osteogenesis in the healing of extraction wounds in dogs; Oral Sug.; 32(6); (Dec. 1971).

Cork et al.; Computer-aided analysis of polarized neurite growth. Effects of applied electrical fields on neuronal development. J Neurosci Methods 32, 45-54 (Apr. 1990).

Courtney et al.; A thoracic mechanism of mild traumatic brain injury due to blast pressure waves. Med Hypotheses 72, 76-83 (Jan. 2009).

Csuka et al.; IL-10 levels in cerebrospinal fluid and serum of patients with severe traumatic brain injury: relationship to IL-6, TNF-alpha, TGF-beta1 and blood-brain barrier function. J Neuroimmunol 101, 211-21 (Nov. 1999).

De Olmos et al.; Use of an amino-cupric-silver technique for the detection of early and semiacute neuronal degeneration caused by neurotoxicants, hypoxia, and physical trauma. Neurotoxicol Teratol 16, 545-61 (Nov. 1994).

Dixon et al.; A controlled cortical impact model of traumatic brain injury in the rat. J Neurosci Methods 39, 253-62 (Oct. 1991).

Dixon et al.; A fluid percussion model of experimental brain injury in the rat. J Neurosurg 67, 110-9 (Jul. 1987).

Edwards et al.; Final results of MRC CRASH, a randomised placebo controlled trial of intravenous corticosteroid in adults with head injury—outcomes at 6 months. Lancet 365, 1957-9 (Jun. 2005).

Elder et al.; Blast-related mild traumatic brain injury: mechanisms of injury and impact on clinical care. Mt Sinai J Med 76, 111-8 (Apr. 2009).

Elder et al.; Increased locomotor activity in mice lacking the low-density lipoprotein receptor. Behav Brain Res 191, 256-65 (Aug. 2008).

Fabre et al.; Antidepressant efficacy and cognitive effects of repetitive transcranial magnetic stimulation in vascular depression: an open trial. Int J Geriatr Psychiatry 19, 833-42 (Sep. 2004).

Farndale et al.; The action of pulsed magnetic fields on cyclic AMP levels in cultured fibroblasts. Biochim Biophys Acta 881, 46-53 (Mar. 19, 1986).

Farrarelli et al.; Breakdown in cortical effective connectivity during midazolam-induced loss of consciousness. Proc Nati Acad Sci U S A 107, 2681-6 (Feb. 9, 2010).

Fassbender et al.; Temporal profile of release of interleukin-1beta in neurotrauma. Neurosci Lett 284, 135-8 (Apr. 2000).

Faul et al.; Traumatic brain injury in the United States (Emergency department visits, hospitalization and deaths 2002-2006); U.S. Dept. of Health and Human Services, 74 pgs.; Mar. 2010.

Fetler et al.; Brain under surveillance: the microglia patrol. Science 309, 392-3 ( Jul. 15, 2005).

Fitzsimmons et al.; A pulsing electric field (PEF) increases human chondrocyte proliferation through a transduction pathway involving nitric oxide signaling. J Orthop Res 26, 854-9 (Jun. 2008).

Foda et al.; A new model of diffuse brain injury in rats. Part II: Morphological characterization. J Neurosurg 80, 301-13 (Feb. 1994).

Foley-Nolan et al.; Pulsed high frequency (27MHz) electromagnetic therapy for persistent neck pain. A double blind, placebo-controlled study of 20 patients. Orthopedics 13, 445-51 (Apr. 1990).

Friedman et al.; Quantitative proton MRS predicts outcome after traumatic brain injury. Neurology 52, 1384-91 (Apr. 1999).

Fukada et al.; On the piezoelectric effect of bone. J Phys Soc Japan 12 (10), 1158-1162 (Oct. 1957).

Gaetz, M.; the neurophysiology of brain injury. Clin Neurophysiol 115, Jan. 4-18, 2004.

Garthwaite et al.; Cyclic GMP and cell death in rat cerebellar slices. Neuroscience 26, 321-6 (Jul. 1988).

Gasparovic et al.; Decrease and recovery of N-acetylaspartate/creatine in rat brain remote from focal injury. J Neurotrauma 18, 241-6 (Mar. 2001).

Ghirnikar et al.; Inflammation in traumatic brain injury: role of cytokines and chemokines. Neurochem Res 23, 329-40 (Mar. 1998).

Glass et al.; Mechanisms underlying inflammation in neurodegeneration. Cell 140, 918-34 (Mar. 19, 2010).

Gona et al.; Effects of 60 Hz electric and magnetic fields on the development of the rat cerebellum. Bioelectromagnetics 14, 433-47 (mo. unavailable) (1993).

Goodwin et al.; A double-blind study of capacitively coupled electrical stimulation as an adjunct to lumbar spinal fusions(printed from online source). Spine 24(13), 1349-1357 (Jul. 1999).

Graeber et al.; New expression of myelomonocytic antigens by microglia and perivascular cells following lethal motor neuron injury. J Neuroimmunol 27, 121-32 (May 1990).

Greenebaum et al.; Effects of pulsed magnetic fields on neurite outgrowth from chick embryo dorsal root ganglia. Bioelectromagnetics 17, 293-302 (mo. unavailable) (1996).

Hart, F.; A quantum mechanical model for bioelectromagnetic resonance phenomena; J Bioelectr; vol. 9; pp. 1-7; Jan. 1990.

Hellmich et al.; Dose-dependent neuronal injury after traumatic brain injury; Brain Research; 1044; pp. 144-154 (May 2005).

Hutchinson et al.; Inflammation in human brain injury: intracerebral concentrations of IL-1alpha, IL-1beta, and their endogenous inhibitor IL-1ra. J Neurotrauma 24, 1545-57 (Oct. 2007).

Ignarro et al.; Heme-dependent activation of guanylate cyclase by nitric oxide: a novel signal transduction mechanism. Blood Vessels 28, 67-73 (Nov.-Dec. 1991).

Ito et al.; Characterization of edema by diffusion-weighted imaging in experimental traumatic brain injury. J Neurosurg 84, 97-103 (Jan. 1996).

Jackson et al.; The demonstration of new human brain-specific proteins by high-resolution two-dimensional polyacrylamide gel electrophoresis. J Neurol Sci 49, 429-38; (Mar. 1981).

Jenrow et al.; Weak ELF magnetic field effects on hippocampal rhythmic slow activity. Exp Neurol 153, 328-34 (Oct. 1998).

Jokela et al.; Assessment of the magnetic field exposure due to the battery current of digital mobile phones. Health Phys 86, 56-66 (Jan. 2004).

Jones et al.; Low energy time varying electromagnetic field interactions with cellular control mechanisms; In: fMechanistic approaches to interactions of electric and electromagnetic fields with living systemsf; Blank, Findl (eds); Plenum Press; NY; pp. 389-397; Oct. 31, 1987.

Jortner, B. S.; The return of the dark neuron. A histological artifact complicating contemporary neurotoxicologic evaluation. Neurotoxicology 27, 628-34 (Jul. 2006).

Kamm et al.; The effect of traumatic brain injury upon the concentration and expression of interleukin-1beta and interleukin-10 in the rat. J Trauma 60, 152-7 (Jan. 2006).

Kanje et al.; Pretreatment of rats with pulsed electromagnetic fields enhances regeneration of the sciatic nerve. Bioelectromagnetics 14, 353-9 (mo. unavailable) (1993).

Kingham et al.; Microglial secreted cathepsin B induces neuronal apoptosis. J Neurochem 76, 1475-84 (Mar. 2001).

Kjellbom et al.; Preparation and polypeptide composition of chlorophyll-free plasma membranes from leaves of light-grown spinach and barley; Physiol Plant; vol. 62; pp. 501-509; Dec. 1984.

Knowles et al.; Nitric oxide synthases in mammals. Biochem J 298, 249-58 (Mar. 1994).

Kossmann et al.; Intrathecal and serum interleukin-6 and the acute-phase response in patients with severe traumatic brain injuries. Shock 4, 311-7 (Nov. 1995).

Kramarenko et al.; Effects of high-frequency electromagnetic fields on human EEG: a brain mapping study. Int J Neurosci 113, 1007-19 (Jul. 2003).

Lai et al.; Magnetic-field-induced DNA strand breaks in brain cells of the rat. Environ Health Perspect 112, 687-94 (May 2004).

Langlois et al.; The epidemiology and impact of traumatic brain injury: a brief overview. J Head Trauma Rehabil 21, 375-8 (Aug. 2006).

Lednev, V.; Possible mechanism for the effect of weak magnetic fields on biological systems: Correction of the basic expression and its consequences; In: Electricity and magnetism in biology and medicine Blank (eds.); San Francisco, CA; San Francisco Press, Inc.; pp. 550-552; Oct. 1993.

Lednev, V.; Possible mechanism for the influence of weak magnetic fields on biological systems; Bioelectromagnetics; vol. 12; pp. 71-75; (mo. unavailable) 1991.

LeDoux, J.; Emotion: clues from the brain. Annu Rev Psychol 46, 209-35 (Jan. 1995).

Lee et al.; Nitric oxide in the healing wound: a time-course study. J Surg Res 101, 104-8 (Nov. 2001).

Lee et al.; Pulsed magnetic and electromagnetic fields in experimental achilles tendonitis in the rat: a prospective randomized study. Arch Phys Med Rehabil 78, 399-404 (Apr. 1997).

Lescot et al.; Temporal and regional changes after focal traumatic brain injury. J Neurotrauma 27, 85-94 (Jan. 2010).

Liboff, et al.; Experimental evidence for ion cyclotron resonance mediation of membrane transport; In: Blank, Findl (eds.); Mechanical approaches to interactions of electric and electromagnetic fields with living systems; Blank, Findl (eds.); New York; Plenum Press; pp. 281-296; Oct. 31, 1987.

Lighthall, J. W.; Controlled cortical impact: a new experimental brain injury model. J Neurotrauma 5, 1-15 (mo. unavailable) (1988).

Lincoln et al.; Low frequency of pathogenic mutations in the ubiquitin carboxy-terminal hydrolase gene in familial Parkinson's disease. Neuroreport 10, 427-9 (Feb. 1999).

Ling et al.; Explosive blast neurotrauma. J Neurotrauma 26, 815-25 (Jun. 2009).

Linovitz et al.; Combined magnetic fields accelerate and increase spine fusion: a double-blind, randomized, placebo controlled study(printed from online source). Spine 27, 1383-1389 (Jul. 2002).

Liu et al.; Ubiquitin C-terminal hydrolase-L1 as a biomarker for ischemic and traumatic brain injury in rats (Author Manuscript). Eur J Neurosci 31(4), 722-32 (Feb. 2010).

Louin et al.; Selective inhibition of inducible nitric oxide synthase reduces neurological deficit but not cerebral edema following traumatic brain injury. Neuropharmacology 50, 182-90 (Feb. 2006).

Maas et al.; Moderate and severe traumatic brain injury in adults. Lancet Neurol 7, 728-41 (Aug. 2008).

Maas et al.; Prognosis and clinical trial design in traumatic brain injury: the IMPACT study. J Neurotrauma 24, 232-8 (Feb. 2007).

Maas et al.; Why have recent trials of neuroprotective agents in head injury failed to how convincing efficacy? A pragmatic analysis and theoretical considerations. (printed from online source) Neurosurgery 44, 1286-98 (Jun. 1999).

Madhusoodanan et al.; NO-cGMP signaling and regenerative medicine involving stem cells. Neurochem Res 32, 681-94 (Apr.-May 2007).

Maeda et al.; Effect of water on piezoelectric, dielectric, and elastic properties of bone; Biopolymers 21(10); 2055-2068 (Oct. 1982).

Marmarou et al.; A new model of diffuse brain injury in rats. Part I: Pathophysiology and biomechanics. J Neurosurg 80, 291-300 (Feb. 1994).

Martin et al.; Parkinson's disease alpha-synuclein transgenic mice develop neuronal mitochondrial degeneration and cell death. J Neurosci 26, 41-50 (Jan. 2006).

McFarlane et al.; Changes in neurite outgrowth but not in cell division induced by low EMF exposure: influence of field strength and culture conditions on responses in rat PC12 pheochromocytoma cells. Bioelectrochemistry 52, 23-8 (Sep. 2000).

McIntosh et al.; Traumatic brain injury in the rat: characterization of a lateral fluid-percussion model. Neuroscience 28(1), 233-44 (mo. unavailable) (1989).

McIntosh et al.; Traumatic brain injury in the rat: characterization of a midline fluid-percussion model. Cent Nery Syst Trauma 4, 119-34 (mo. unavailable) (1987).

Mellor, S.; The pathogenesis of blast injury and its management. Br J Hosp Med 39, 536-9 (Jun. 1988).

Mont et al.; Pulsed electrcial stimulation to defer TKA in patients with knee osteoarthritis; The Cutting Edge; 29(10); pp. 887-892 (Oct. 2006).

Morganti-Kossmann et al.; Production of cytokines following brain injury: beneficial and deleterious for the damaged tissue. Mol Psychiatry 2, 133-6 (Mar. 1997).

Morris et al.; Place navigation impaired in rats with hippocampal lesions. Nature 297, 681-3 (Jun. 1982).

Naldini et al.; Role of inflammatory mediators in angiogenesis. Curr Drug Targets Inflamm Allergy 4, Feb. 3-8, 2005.

Nara, et al.; Fourier Transform Infrared Spectroscopic Study on the Ca2+-bound Coordination Structures of Synthetic Peptide Analogues of the Calcium-binding Site III of Troponin C; Biopolymers; vol. 82; issue 4; pp. 339-343; Jul. 2006.

Narayan et al.; Clinical trials in head injury (Author Manuscript). J Neurotrauma 19, 503-57 (May 2002).

Nauta et al.; Silver impregnation of degenerating axons in the central nervous system: a modified technic. Stain Technol 29, 91-3 (Mar. 1954).

Northington et al.; Early Neurodegeneration after Hypoxia-Ischemia in Neonatal Rat Is Necrosis while Delayed Neuronal Death Is Apoptosis. Neurobiol Dis 8, 207-19 (Apr. 2001).

Oda et al.; Magnetic field exposure saves rat cerebellar granule neurons from apoptosis in vitro. Neurosci Lett 365, 83-6 (Jul. 22, 2004).

Ohkubo et al.; Acute effects of static magnetic fields on cutaneous microcirculation in rabbits; In Vivo; vol. 11; pp. 221-226; May-Jun. 1997.

Okano et al.; Biphasic effects of static magnetic fields on cutaneous microcirculation in rabbits; Bioelectromagnetics; vol. 20(3); pp. 161-171; (mo. unavailable) 1999.

Okie, S.; Traumatic brain injury in the war zone. N Engi J Med 352, 2043-7 (May 19, 2005).

Olbe et al.; The spinach plasma membrane Ca2p pump is a 120-kDa polypeptide regulated by calmodulinbinding to a terminal region; Physiol Plantarum; vol. 103; pp. 35-44; May 1998.

Pantazis et al.; The nitric oxide-cyclic GMP pathway plays an essential role in both promoting cell survival of cerebellar granule cells in culture and protecting the cells against ethanol neurotoxicity. J Neurochem 70, 1826-38 (May 1998).

Papa et al.; Ubiquitin C-terminal hydrolase is a novel biomarker in humans for severe traumatic brain injury. Crit Care Med 38, 138-44 (Jan. 2010).

Pascual et al.; Time course of early metabolic changes following diffuse traumatic brain injury in rats as detected by (1)H NMR spectroscopy. J Neurotrauma 24, 944-59 (Jun. 2007).

Patino et al.; Pulsed electromagnetic fields in experimental cutaneous wound healing in rats. J Burn Care Rehabil 17, 528-31 (Nov./Dec. 1996).

Paylor et al.; Inbred strain differences in prepulse inhibition of the mouse startle response. Psychopharmacology (Berl) 132, 169-80 (Jul. 1997).

Pennington et al.; Pulsed, non-thermal, high-frequency electromagnetic energy (DIAPULSE) in the treatment of grade I and grade II ankle sprains. Mil Med 158, 101-4 (Feb. 1993).

Pfeffer et al.; Disturbed sleep/wake rhythms and neuronal cell loss in lateral hypothalamus and retina of mice with a spontaneous deletion in the ubiquitin carboxyl-terminal hydrolase L1 gene. Neurobiol Aging 33, 393403, in press, Epub ahead of print (Apr. 2010).

Pilla et al.; Gap junction impedance tissue dielectrics and thermal noise limits for electromagnetic field bioeffects; Bioelectrochemistry and Bioenergetics; vol. 35; pp. 63-69; Nov. 1994.

Pilla, A.; Mechanisms and therapeutic applications of time-varying and static magnetic fields; In: Biological and Medical Aspects of Electromagnetic Fields (eds. Barnes et al.) CRC Press, Boca Raton FL, 351-411 (Oct. 2006).

Pilla; Electrochemical information and energy transfer in vivo; Proc. 7th IECEC; Washington, D.C.; American Chemical Society; pp. 761-64; (mo. unavailable) 1972.

Pineros et al.; Calcium channels in higher plant cells: Selectivity, regulation, and pharmacology; J Exp Bot; vol. 48; special issue; pp. 551-577; Mar. 1971.

Pirozzoli et al.; Effects of 50 Hz electromagnetic field exposure on apoptosis and differentiation in a neuroblastoma cell line. Bioelectromagnetics 24, 510-6 (Oct. 2003).

Ramundo-Orlando, et al.; Effect of Low Frequency, Low Amplitude Magnetic Fields on the Permeability of Cationic Liposomes Entrapping Carbonic Anhydrase I. Evidence for Charged Lipid Involvement; Bioelectromagnetics; vol. 21; pp. 491-498; Oct. 2000.

Reale et al.; Modulation of MCP-1 and iNOS by 50-Hz sinusoidal electromagnetic field. Nitric Oxide 15, 50-7 (Aug. 2006).

Ren et al.; Role of interleukin-1? during pain and inflammation (Author Manuscript). Brain Res Rev 60, 57-64 (Apr. 2009).

Rich et al.; Chronic caloric restriction reduces tissue damage and improves spatial memory in a rat model of traumatic brain injury. J Neurosci Res 88, 2933-9 (Oct. 2010).

Rogers et al.; Behavioral and functional analysis of mouse phenotype: Shirpa, a proposed protocol for comprehensive phenotype assessment. Mamm Genome 8, 711-3 (Oct. 1997).

Rohde et al.; Effects of pulsed electromagnetic fields on interleukin-1 beta and postoperative pain: a double-blind, placebo-controlled, pilot study in breast reduction patients. Plast Reconstr Surg 125, 1620-9 (Jun. 2010).

Sagan, L.; Epidemiological and laboratory studies of power frequency electric and magnetic fields; JAMA; vol. 268(5); pp. 625-629; Aug. 5, 1992.

Saljo et al.; Exposure to short-lasting impulse noise causes microglial and astroglial cell activation in the adult rat brain. Pathophysiology 8, 105-111 (Dec. 2001).

Saljo et al.; Low-level blast raises intracranial pressure and impairs cognitive function in rats: prophylaxis with processed cereal feed. J Neurotrauma 27, 383-9 (Feb. 2010).

Salzberg et al.; The effects of non-thermal pulsed electromagnetic energy on wound healing of pressure ulcers in spinal cord-injured patients: a randomized, double-blind study. Ostomy Wound Manage 41, 42-4, 46, 48 passim (Apr. 1995).

Sandyk, R.; Treatment with AC pulsed electromagnetic fields improves olfactory function in Parkinson's disease. Int J Neurosci 97, 225-33 (Apr. 1999).

Sapolsky; Glucocorticoid toxicity in the hippocampus: temporal aspects of neuronal vulnerability. Brain Res 359, 300-5 (Dec. 16, 1985).

Sarimov, et al.; Exposure to ELF Magnetic Field Tuned to ZN Inhibits Growth of Cancer Cells. Bioelectromagnetics; vol. 26; No. 8; pp. 631-638; Dec. 2005.

Sauerland et al.; Risks and benefits of preoperative high dose methylprednisolone in surgical patients: a systematic review. Drug Saf 23, 449-61 (Nov. 2000).

Schmued et al.; Fluoro-Jade: a novel fluorochrome for the sensitive and reliable histochemical localization of neuronal degeneration. Brain Res 751, 37-46 (Mar. 1997).

Seegers et al.; Activation of signal-transduction mechanisms may underlie the therapeutic effects of an applied electric field. Med Hypotheses 57, 224-30 (Aug. 2001).

Shupak et al.; Human exposure to a specific pulsed magnetic field: effects on thermal sensory and pain thresholds. Neurosci Lett 363, 157-62 (Jun. 10, 2004).

Slepko et al.; Progressive activation of adult microglial cells in vitro. Glia 16, 241-46 (Mar. 1996).

Smith, S.; Calcium cyclotron resonance and diatom mobility; Bioelectromagnetics; vol. 8; pp. 215-227; (mo. unavailable) 1987.

Stahel et al.; The role of the complement system in traumatic brain injury. Brain Res Brain Res Rev 27, 243-56 (Jul. 1998).

Steinberg et al.; Results of core decompression and grafting with and without electrical stimulation. Clin Orthop, 199-208 (Dec. 1989).

Tehranian et al.; Improved recovery and delayed cytokine induction after closed head injury in mice with central overexpression of the secreted isoform of the interleukin-1 receptor antagonist. J Neurotrauma 19, 939-51 (Aug. 2002).

Terpolilli et al.; The novel nitric oxide synthase inhibitor 4-aminotetrahydro-L-biopterine prevents brain edema formation and intracranial hypertension following traumatic brain injury in mice. J Neurotrauma 26, 1963-75 (Nov. 2009).

Thurman et al.; The epidemiology of sports-related traumatic brain injuries in the United States: recent developments. J Head Trauma Rehabil 13, Apr. 1-8, 1998.

Trillo et al.; Magnetic fields at resonant conditions for the hydrogen ion affect neurite outgrowth in PC-12 cells: a test of the ion parametric resonance model. Bioelectromagnetics 17, 10-20 (mo. unavailable) (1996).

Unterberg et al.; Edema and brain trauma. Neuroscience 129(4), 1021-9 (mo. unavailable) (2004).

Vianale et al.; Extremely low frequency electromagnetic field enhances human keratinocyte cell growth and decreases proinflammatory chemokine production. Br J Dermatol 158(6), 1189-96 (Jun. 2008).

Weinstein, et al.; Ca2+-Binding and Structural Dynamics in the functions of Calmodulin; Ann. Rev. Physiol; vol. 56; pp. 213-236; Mar. 1994.

Weintraub, M.; Magnetic bio-stimulation in painful diabetic peripheral neuropathy: a novel intervention R a randomized double-placebo crossover study; Am J Pain Manag; vol. 9; pp. 8-17; Jan. 1, 1999.

Weissman et al.; Activation and inactivation of neuronal nitric oxide synthase: characterization of Ca(2+)-dependent [125I]Calmodulin binding. Eur J Pharmacol 435, Jan. 9-18, 2002).

Wenk, G.; The nucleus basalis magnocellularis cholinergic system: one hundred years of progress; Neurobiology of Learning and Memory; 67(2); 85-95 (Mar. 1997).

Williams et al.; Characterization of a new rat model of penetrating ballistic brain injury. J Neurotrauma 22, 313-31 (Feb. 2005).

Yasuda, I.; Part III. Clinical Studies: Mechanical and electrical callus; Annals of the New York Academy of Sciences; vol. 238; pp. 457-465 (Oct. 1974).

Yu et al.; Effects of 60 Hz electric and magnetic fields on maturation of the rat neopallium. Bioelectromagnetics 14, 449-58 (mo. unavailable) (1993).

Yumoto, et al.; Coordination Structures of Ca2+ and Mg2+ in Akazara Scallop Troponin C in Solution; Eur. J. Biochem; vol. 268(23); pp. 6284-6290; Dec. 2001.

Zaloshnja et al.; Prevalence of long-term disability from traumatic brain injury in the civilian population of the United States, 2005. J Head Trauma Rehabil 23, 394-400 (Nov./Dec. 2008).

Zhadin, et al.; Frequency and Amplitude Windows in the Combined Action of DC and Low Frequency AC Magnetic Fields on Ion Thermal Motion in a Macromolecule: Theoretical Analysis; Bioelectromagnetics; vol. 26; issue 4; pp. 323-330; May 2005.

Ziebell et al.; Involvement of pro- and anti-inflammatory cytokines and chemokines in the pathophysiology of traumatic brain injury. Neurotherapeutics 7, Jan. 22-30, 2010.

Zizic et al.; The treatment of osteoarthritis of the knee with pulsed electrical stimulation. J Rheumatol 22, 1757-61 (Sep. 1995).

\* cited by examiner

Haecker Implant Measured at one half inch above the highest point. Numbers in circles represent the percentage difference from the base line.

Haecker Implant Measured at one half inch above the highest point. Numbers in circles represent the percentage difference from the base line.

DePUY Implant Measured at one half inch above the highest point. Numbers in circles represent the percentage difference from the base line.

DePUY Implant Measured at one half inch above the highest point. Numbers in circles represent the percentage difference from the base line.

| R (Inch) | Θ (Deg) | Base Line mVp-p | BioMet Knee Height = 0.125 inch Meas mVp-p | Change mVp-p | Change % | BioMet Knee Height = 0.625 inch Meas mVp-p | Change mVp-p | Change % | DePuy Knee Height = 0.125 inch Meas mVp-p | Change mVp-p | Change % | DePuy Knee Height = 0.625 inch Meas mVp-p | Change mVp-p | Change % |
|---|---|---|---|---|---|---|---|---|---|---|---|---|---|---|
| 0 | 0 | 230 | 194 | -36 | -15.7% | 198 | -32 | -13.9% | 186 | -44 | -19.1% | 184 | -46 | -20.0% |
| 1 | 0 | 242 | 224 | -18 | -7.4% | 229 | -13 | -5.4% | 204 | -38 | -15.7% | 210 | -32 | -13.2% |
| 2 | 0 | 290 | 282 | -8 | -2.8% | 284 | -6 | -2.1% | 266 | -24 | -8.3% | 264 | -26 | -9.0% |
| 3 | 0 | 460 | 444 | -16 | -3.5% | 442 | -18 | -3.9% | 424 | -36 | -7.8% | 418 | -42 | -9.1% |
| 1 | 45 | 240 | 220 | -20 | -8.3% | 224 | -16 | -6.7% | 204 | -36 | -15.0% | 204 | -36 | -15.0% |
| 2 | 45 | 280 | 276 | -4 | -1.4% | 274 | -6 | -2.1% | 254 | -26 | -9.3% | 252 | -28 | -10.0% |
| 3 | 45 | 394 | 394 | 0 | 0.0% | 392 | -2 | -0.5% | 362 | -32 | -8.1% | 362 | -32 | -8.1% |
| 1 | 90 | 234 | 218 | -16 | -6.8% | 222 | -12 | -5.1% | 194 | -40 | -17.1% | 200 | -34 | -14.5% |
| 2 | 90 | 274 | 276 | 2 | 0.7% | 274 | 0 | 0.0% | 256 | -18 | -6.6% | 252 | -22 | -8.0% |
| 3 | 90 | 406 | 408 | 2 | 0.5% | 404 | -2 | -0.5% | 372 | -34 | -8.4% | 386 | -20 | -4.9% |
| 1 | 135 | 234 | 188 | -46 | -19.7% | 210 | -24 | -10.3% | 132 | -102 | -43.6% | 176 | -58 | -24.8% |
| 2 | 135 | 274 | 288 | 14 | 5.1% | 276 | 2 | 0.7% | 266 | -8 | -2.9% | 248 | -26 | -9.5% |
| 3 | 135 | 406 | 410 | 4 | 1.0% | 404 | -2 | -0.5% | 390 | -16 | -3.9% | 388 | -18 | -4.4% |
| 1 | 180 | 236 | 128 | -108 | -45.8% | 184 | -52 | -22.0% | 110 | -126 | -53.4% | 156 | -80 | -33.9% |
| 2 | 180 | 280 | 262 | -18 | -6.4% | 264 | -16 | -5.7% | 152 | -128 | -45.7% | 204 | -76 | -27.1% |
| 3 | 180 | 416 | 432 | 16 | 3.8% | 422 | 6 | 1.4% | 398 | -18 | -4.3% | 378 | -38 | -9.1% |
| 1 | 225 | 240 | 144 | -96 | -40.0% | 192 | -48 | -20.0% | 138 | -102 | -42.5% | 178 | -62 | -25.8% |
| 2 | 225 | 288 | 294 | 6 | 2.1% | 276 | -12 | -4.2% | 290 | 2 | 0.7% | 258 | -30 | -10.4% |
| 3 | 225 | 444 | 464 | 20 | 4.5% | 452 | 8 | 1.8% | 426 | -18 | -4.1% | 428 | -16 | -3.6% |
| 1 | 270 | 240 | 210 | -30 | -12.5% | 218 | -22 | -9.2% | 204 | -36 | -15.0% | 204 | -36 | -15.0% |
| 2 | 270 | 290 | 292 | 2 | 0.7% | 288 | -2 | -0.7% | 268 | -22 | -7.6% | 264 | -26 | -9.0% |
| 3 | 270 | 448 | 450 | 2 | 0.4% | 452 | 4 | 0.9% | 416 | -32 | -7.1% | 412 | -36 | -8.0% |
| 1 | 315 | 240 | 226 | -14 | -5.8% | 228 | -12 | -5.0% | 208 | -32 | -13.3% | 242 | 2 | 0.8% |
| 2 | 315 | 286 | 284 | -2 | -0.7% | 286 | 0 | 0.0% | 266 | -20 | -7.0% | 262 | -24 | -8.4% |
| 3 | 315 | 442 | 442 | 0 | 0.0% | 442 | 0 | 0.0% | 410 | -32 | -7.2% | 422 | -20 | -4.5% |

FIG. 32

METHODS AND DEVICES FOR PROVIDING ELECTROMAGNETIC TREATMENT IN THE PRESENCE OF A METAL-CONTAINING IMPLANT

CROSS REFERENCE TO RELATED APPLICATIONS

This patent application does not claim priority to any other patent application.

This application may be related to any of the following patent applications, each of which is herein incorporated by reference in its entirety: U.S. application Ser. No. 11/003,108, titled "APPARATUS AND METHOD FOR ELECTROMAGNETIC TREATMENT OF PLANT, ANIMAL AND HUMAN TISSUE, ORGANS, CELLS AND MOLECULES" filed on Dec. 3, 2004 (now U.S. Pat. No. 7,744,524); U.S. application Ser. No. 12/771,954, titled "APPARATUS AND METHOD FOR ELECTROMAGNETIC TREATMENT OF PLANT, ANIMAL AND HUMAN TISSUE, ORGANS, CELLS AND MOLECULES" filed on Apr. 30, 2010 (now US Publication No. US-2010-0210893-A1); U.S. application Ser. No. 12/772,002, titled "APPARATUS AND METHOD FOR ELECTROMAGNETIC TREATMENT OF PLANT, ANIMAL AND HUMAN TISSUE, ORGANS, CELLS AND MOLECULES" filed on Apr. 30, 2010 (now US Publication No. US-2010-0222631-A1); U.S. application Ser. No. 12/819,956, titled "APPARATUS AND METHOD FOR ELECTROMAGNETIC TREATMENT" filed on Jun. 21, 2010 (now US Publication No. US-2011-0112352-A1); U.S. application Ser. No. 11/114,666, titled "ELECTROMAGNETIC TREATMENT INDUCTION APPARATUS AND METHOD FOR USING SAME" filed on Apr. 26, 2005 (now U.S. Pat. No. 7,740,574); U.S. application Ser. No. 11/223,073, titled "INTEGRATED COIL APPARATUS FOR THERAPEUTICALLY TREATING HUMAN AND ANIMAL CELLS, TISSUES AND ORGANS WITH ELECTROMAGNETIC FIELDS AND METHOD FOR USING SAME" filed on Sep. 10, 2005 (now U.S. Pat. No. 7,758,490); U.S. application Ser. No. 12/082,944, titled "ELECTROMAGNETIC FIELD TREATMENT APPARATUS AND METHOD FOR USING SAME" filed on Apr. 14, 2008 (now U.S. Pat. No. 7,896,797); U.S. Provisional Application No. 61/389,038, titled "PULSED ELECTROMAGNETIC FIELDS (PEMF) FOR THE TREATMENT OF TRAUMATIC BRAIN INJURY" filed on Oct. 1, 2010; U.S. Provisional Application No. 61/456,310, titled "METHOD AND APPARATUS FOR ELECTROMAGNETIC TREATMENT OF HEAD, CEREBRAL AND NEURAL INJURY IN ANIMALS AND HUMANS" filed on Nov. 4, 2010; U.S. application Ser. No. 13/252,114, titled "METHOD AND APPARATUS FOR ELECTROMAGNETIC TREATMENT OF HEAD, CEREBRAL AND NEURAL INJURY IN ANIMALS AND HUMANS" filed on Oct. 3, 2011; U.S. application Ser. No. 13/285,761, titled "METHOD AND APPARATUS FOR ELECTROMAGNETIC ENHANCEMENT OF BIOCHEMICAL SIGNALING PATHWAYS FOR THERAPEUTICS AND PROPHYLAXIS IN PLANTS, ANIMALS AND HUMANS" filed on Oct. 31, 2011.

INCORPORATION BY REFERENCE

All publications and patent applications mentioned in this specification are herein incorporated by reference to the same extent as if each individual publication or patent application was specifically and individually indicated to be incorporated by reference.

FIELD

Described herein are electromagnetic treatment devices, systems and methods pertaining generally to the therapeutic treatment of subjects having a metal-containing implant, such as a prosthetic in the region of the tissue to be treated. In particular, described herein are methods for calibrating electromagnetic delivery devices so that the devices can provide a therapeutic magnetic field in the presence of a metal-containing implant, as well as calibrated electromagnetic treatment devices adapted for use with, or near, metal-containing implants. Also described are electromagnetic field (EMF) devices and methods for post-operative treatment to promote healing and repair of a subject's operation site in proximity to a metal-containing implant. An embodiment according to the present invention pertains to use of non-thermal time-varying EMF, adapted for use with metal-containing implants, and configured to accelerate the asymmetrical kinetics of the binding of intracellular ions to their respective buffers which regulate the biochemical signaling pathways living systems employ for growth, repair and maintenance. Further embodiments provide wearable treatment delivery devices having structural support member(s) designed to maintain the integrity of the delivered EMF.

BACKGROUND

Over the past 40 years, it has been found that the application of weak non-thermal electromagnetic fields ("EMF") can result in physiologically meaningful in vivo and in vitro bio-effects. Time-varying electromagnetic fields, comprising EMF, ranging from several Hertz to about 100 GHz, have been found to be clinically beneficial when used as a therapy for reducing pain levels for patients undergoing surgical procedures, promoting healing in patients with chronic wounds or bone fractures, and reducing inflammation or edema in injuries (e.g. sprains).

Presently several EMF devices constitute the standard armamentarium of orthopaedic clinical practice for treatment of difficult to heal fractures. The success rate for these devices has been very high. The database for this indication is large enough to enable its recommended use as a safe, non-surgical, non-invasive alternative to a first bone graft. Additional clinical indications for these technologies have been reported in double blind studies for treatment of avascular necrosis, tendinitis, osteoarthritis, wound repair, blood circulation and pain from arthritis as well as other musculoskeletal injuries.

In addition, cellular studies have addressed effects of weak electromagnetic fields on both signal transduction pathways and growth factor synthesis. It has been shown that EMF stimulates secretion of growth factors after a short, trigger-like duration. Ion/ligand binding processes at intracellular buffers attached to the cell membrane are an initial EMF target pathway structure. The clinical relevance to treatments, for example, of bone repair, is up-regulation such as modulation, of growth factor production as part of normal molecular regulation of bone repair. Cellular level studies have shown effects on calcium ion transport, cell proliferation, Insulin Growth Factor ("IGF-II") release, and IGF-II receptor expression in osteoblasts. Effects on Insulin Growth Factor-I ("IGF-I") and IGF-II have also been demonstrated in rat fracture callus. Pulsed electromagnetic fields ("PEMF") have also been shown to have an effect on transforming growth factor beta ("TGF-β") messenger RNA ("mRNA") in a bone induction model in a rat. Studies have also demonstrated up-regulation of TGF-β mRNA by PEMF in human osteoblast-like cell line designated MG-63, wherein there were increases in TGF-β1, collagen, and osteocalcin synthesis. PEMF stimulated an increase in TGF-β1 in both hypertrophic and atrophic cells from human non-union tissue.

Further studies demonstrated an increase in both TGF-β1 mRNA and protein in osteoblast cultures resulting from a direct effect of EMF on a calcium/calmodulin-dependent pathway. Cartilage cell studies have shown similar increases in TGF-β1 mRNA and protein synthesis from EMF, demonstrating a therapeutic application to joint repair. U.S. Pat. No. 4,315,503 (1982) to Ryaby, U.S. Pat. No. 7,468,264 (2008) to Brighton and U.S. Pat. Nos. 5,723,001 (1998) and 7,744,524 (2010) to Pilla typify the research conducted in this field.

Despite the promising developments in EMF treatment, EMF therapies have been largely limited to treating patients without metal-containing implants or prosthetics. This is primarily because the much higher conductivity of metals, compared to tissue and body fluids, can reduce the desired EMF dosage for patient treatment, and/or alter the distribution, uniformity or pattern of the applied EMF. For example, the metal in joint implants may preferentially absorb or otherwise alter the shape of an applied electromagnetic field, which reduces the strength and range of the field. As such, beneficial EMF treatments have not been provided to the majority of patients undergoing procedures (such as knee or shoulder replacement) where metal-containing implants or prosthetics are used.

Accordingly, some embodiments described herein address the need for electromagnetic therapy devices (e.g., PEMF devices) that are compatible with metal implants, and provide methods for calibrating EMF delivery devices (e.g., "detuning") such that the EMF devices can provide appropriate EMF treatment to a patient with a metal-containing implant or prosthesis. Additionally, other embodiments described provide EMF delivery devices and treatments to help promote healing and recovery by delivering EMF treatment to a target location in proximity to a metal-containing implant or prosthetic. Furthermore, because patients recovering from surgery often have reduced mobility, other embodiments described provide for easy-to-wear and adjustable EMF delivery devices. The described embodiments can be adjusted to be worn or placed near a target treatment location such as an operation site while accommodating the patient's need for flexibility and comfort.

Another challenge in maintaining the integrity of the electromagnetic field delivered for treatment arises from the EMF device itself. In some cases, the EMF device's own components can lack the requisite durability and resilience to maintain the shape and strength of the needed EMF. For example, EMF delivery devices often employ ductile metal coils or metal wires to deliver an electromagnetic field. Although such materials are advantageous for delivering electromagnetic fields, these materials also have the tendency to break from stress fatigue than can result from repeated bending and flexing, which may naturally occur from use. Moreover, once a coil or wire has been deformed or broken, its delivered EMF may no longer have the strength, shape, or structure appropriate for treatment. Therefore, some embodiments described herein provide for EMF devices having support members to maintain the integrity (e.g. structure, shape, resilience, or strength) of a generated EMF.

SUMMARY OF THE DISCLOSURE

The present invention relates to electromagnetic field treatment devices that are configured or adapted for the application of therapeutic electromagnetic signals (including PEMF) to treat a patient having a metal-containing implant or prosthesis. Included in this description are methods and devices calibrated to accommodate for interference that may occur when treatment is delivered in proximity to a metal-containing implant or prosthesis.

Some embodiments described provide an electromagnetic treatment device for treating living tissue, wherein the device is compatible with a metal-containing implant or prosthesis and includes a control circuit configured to generate an electromagnetic signal and an applicator configured to deliver a calibrated magnetic field, the applicator calibrated to have substantially no inductive reactance and substantially no capacitive reactance when delivering the magnetic field in proximity to the metal prosthesis.

Optionally, in any of the preceding embodiments, the control circuit may be configured to provide an electromagnetic signal to the applicator to induce an electric field of peak amplitude between about 1 $\mu$V/m and about 100 V/m in the target tissue and a peak induced magnetic field between about 1 $\mu$T and about 0.1 T, wherein the signal generated by the control circuit comprises a burst of waveforms having a burst duration of greater than 50 $\mu$sec and a burst repetition rate of about 0.01 to about 1000 bursts per second.

Additionally, in any of the preceding embodiments, the electromagnetic treatment device may further include a tuning circuit. The tuning circuit may also have an impedance value of about 50 ohms at 27.120 MHz.

Optionally, in any of the preceding embodiments, the electromagnetic treatment device may include an applicator comprising a loop applicator.

Other embodiments provide for an electromagnetic treatment device comprising a control circuit configured to generate an electromagnetic signal; an applicator configured to generate a calibrated electromagnetic field; a tuning circuit connected to the applicator, wherein the tuning circuit is configured to substantially eliminate an inductive component of reactance and a capacitance component of reactance of the applicator when the applicator is positioned near a metal implant.

Optionally, in any of the preceding embodiments, the tuning circuit may be coupled to the applicator and include a resistor, an adjustable series capacitor, and an adjustable parallel capacitor. The series capacitor and parallel capacitor may be configured to adjust the reactance of the applicator such that the reactance of the applicator is substantially purely resistive.

Additional embodiments provide for an electromagnetic treatment device comprising an electromagnetic treatment device configured to provide an electromagnetic field to a target treatment location containing a metal-containing implant or prosthesis, the electromagnetic treatment device having an applicator and an adjustable circuit configured to correct electromagnetic interference caused by the metal containing implant or prosthesis by reducing or eliminating an inductive component and a capacitance component of the applicator's reactance when the applicator is in proximity to the metal-containing prosthesis.

Optionally, in any of the preceding embodiments, the circuit of the treatment device can include an adjustable series capacitance and an adjustable parallel capacitance connected to the applicator. Further embodiments provide that the reactance of the applicator's reactance substantially purely resistive.

Optionally, in any of the preceding embodiments, the electromagnetic treatment includes a stiffening member configured to maintain the shape of the applicator.

Optionally, in any of the preceding embodiments, the electromagnetic treatment device has an applicator loop comprising a flexible metal coil.

Another aspect of the invention provides for a method of calibrating an electromagnetic treatment device so that it may be used to treat tissue adjacent to a metal-containing prosthesis. Some embodiments provide that this method includes placing an applicator of the electromagnetic treatment device around or adjacent to a metal material; generating a magnetic field with the applicator; and adjusting a tuning circuit connected to the applicator to substantially eliminate any inductive component and any capacitance component of the applicator when the applicator is near the metal material.

Optionally, in any of the preceding embodiments, the method may include adjusting a series capacitance and a parallel capacitance to substantially eliminate the inductive and capacitance components of a reactance of the applicator. In some variations, adjusting the tuning circuit further results in a substantially purely resistive applicator.

Another aspect of the invention provides for methods of treating patients having a metal-containing implant or prosthesis. Some embodiments provide a method comprising placing a calibrated applicator of an electromagnetic treatment device in proximity to tissue including a metal-containing implant or prosthesis; and delivering an electromagnetic field from the calibrated applicator, wherein the calibrated applicator has a reactance that is substantially purely resistive in the presence of the metal-containing implant or prosthesis.

Optionally, in any of the preceding embodiments, the method may include applying the electromagnetic field to the tissue including a metal-containing prosthesis within 90 days of an implant procedure.

Optionally, in any of the preceding embodiments, the method may also include delivering an electromagnetic field where the electromagnetic field comprises generating at least one burst of sinusoidal, rectangular, chaotic, or random waveforms, having a frequency content in a range of about 0.01 Hz to about 10,000 MHz, having a burst duration from about 0.1 to about 100 msec, inducing a peak amplitude of 0.001 G to about 100 G, and having a burst repetition rate from about 0.01 to about 100 bursts/second.

In some variations, the electromagnetic field comprises a ISM carrier frequency modulated at about a 1 msec to about a 10 msec burst repeating at about 1 Hz to about 10 Hz, inducing a peak amplitude of 0.001 G to about 0.1 G.

In other variations, the electromagnetic field is applied to the tissue for twenty minutes every four hours. In some variations, the filed is applied for 20 minutes on between 3 hours and 40 minutes off.

In further variations, the electromagnetic field is applied for five minutes every twenty minutes.

In other variations, the electromagnetic field is applied for fifteen minutes every hour and forty-five minutes.

In other variations, the electromagnetic field is applied for about 5 minutes to about 30 minutes, repeating at a duty cycle of about 1% to about 25%.

Another aspect of the invention provides for wearable EMF treatment devices. Some embodiments provide an electromagnetic treatment device comprising: a wearable EMF applicator assembly, the assembly comprising a control circuit configured to generate an electromagnetic signal and an applicator configured to deliver an electromagnetic field, the applicator comprising an applicator loop, wherein the loop is a flexible metal wire having a diameter of between about 4 and about 11 inches; a stiffening member coupled to the EMF applicator assembly and configured to resiliently maintain the shape of the loop; and a replaceable power supply configured to releasably connect to the EMF applicator assembly.

Optionally, in any of the preceding embodiments, the electromagnetic treatment device can include at least one adjustable and detachable strap attached to a strap attaching element disposed on the stiffening member.

Optionally, in any of the preceding embodiments, the electromagnetic treatment device can have a flexible metal wire that is in the shape of a bent oval.

Optionally, in any of the preceding embodiments, the electromagnetic treatment device may have a stiffening member made of a molded foam material.

In further embodiments, the stiffening member comprises a EVA and polyolefin foam with a durometer of 70 asker C, density of 400 $kg/m^3$, tensile strength of 38 $Kg/cm^2$, tear strength of 22 $kg/cm^2$, and elongation of 250%.

Optionally, in any of the preceding embodiments, the electromagnetic treatment device further comprises a set of electrical connections configured to electrically and physically connect the EMF applicator assembly with the replaceable power supply.

Optionally, in any of the preceding embodiments, the electromagnetic treatment device has a replaceable battery pack. In some variations the device includes a battery that is rechargeable. For example, in some variations the device includes a battery pack with an activating pull tab. The activating pull tab may minimize the possibility of depleted batteries during storage. In some variations the device includes a memory chip which may store battery data, and an ID which identifies the battery pack. The system or device may require a match between the device and the battery pack. The memory chip may also allow storage of one or more treatment regimens and may be programmed for a maximum limit of the number of treatments per pack. Thus, in some variations, the device may include electrical contacts which interface the power and memory chip to the main electronics.

Optionally, in any of the preceding embodiments, the electromagnetic treatment device includes a display screen and user interface buttons. In some variations, the device includes an audio user interface. Other embodiments provide a display screen configured to display the time remaining for a treatment period where the treatment period can be a period where the EMF delivery device is active or inactive. Additionally, the display screen may be configured to display remaining power supply.

Optionally, in any of the preceding embodiments, the electromagnetic treatment device has an EMF applicator assembly with a pre-programed treatment regimen and/or a manual treatment program.

Optionally, in any of the preceding embodiments, the electromagnetic treatment device can include a memory storage component configured to store treatment data.

In some variations, the electromagnetic treatment device is disposable.

In other variations, the electromagnetic treatment device and applicator are configured to deliver an electromagnetic field to an area near a metal knee implant.

In other variations, the electromagnetic treatment device and applicator are configured to deliver an electromagnetic field to an area near a shoulder implant.

BRIEF DESCRIPTION OF THE DRAWINGS

FIG. 32 is a table showing the results of the measurements for the baseline, BioMet knee implant, and DePuy knee implants.

DETAILED DESCRIPTION

Figure 1:
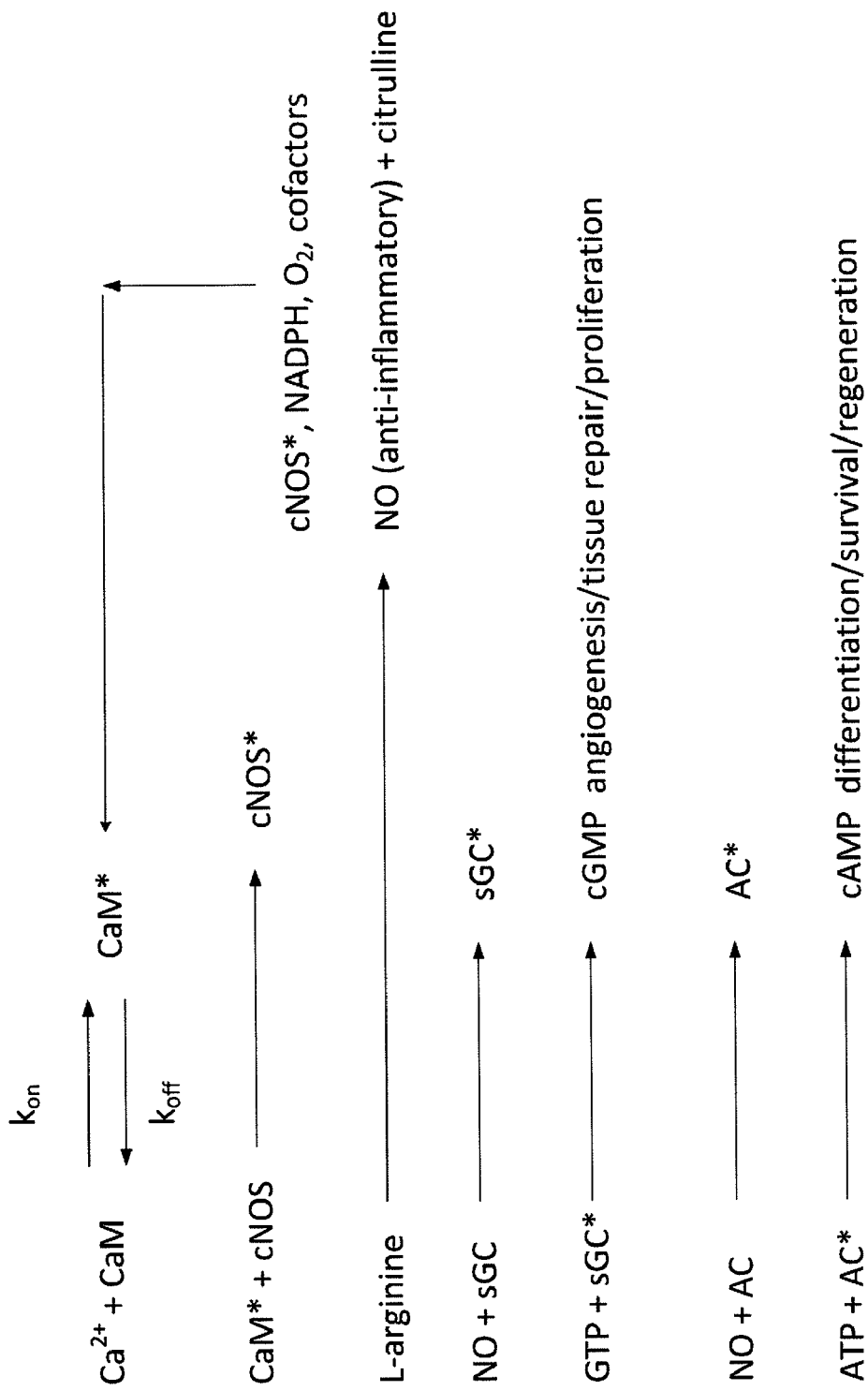
FIG. 1 is a schematic representation of the biological EMF transduction pathway which is a representative target pathway of EMF signals configured according to embodiments described.

Specific details are set forth in the following description and figures to provide an understanding of various embodiments of the invention. Certain well-known details, associated electronics and devices which are not set forth in the following disclosure are omitted only to avoid unnecessarily obscuring the various embodiments of the invention; those of ordinary skill in the relevant art will understand that they can practice other embodiments of the invention without one or more of the details described below. While various processes are described with reference to steps and sequences in the following disclosure, the description is for providing a clear implementation of particular embodiments of the invention, and the steps and sequences of steps should not be taken as required to practice this invention. As described in detail in many of the patent applications previously incorporated by referenced in their entirety, an electromagnetic treatment device (including PEMF devices) may be configured to modulate one or more cellular processes, including driving reactions at cell membranes or within cells. For example, PEMF devices such as those incorporated by reference above may be configured to drive calcium ("$Ca^{2+}$") binding to calmodulin ("CaM"). The specific magnetic fields applied by the PEMF devices may be chosen and calibrated for this purpose and to compensate for when a metal or other potentially interfering material or structure alters or dampens the applied field, making it unlikely that the indended therapeutic effect can be achieved.

By way of background, basal levels of intracellular $Ca^{2+}$ are typically 50-100 nM, tightly maintained by a number of physiological calcium buffers. It is generally accepted that transient elevations in cytosolic $Ca^{2+}$ from external stimuli as simple as changes in temperature and mechanical forces, or as complex as mechanical disruption of tissue, rapidly activate CaM, which equally rapidly activates the cNOS enzymes, i.e., endothelial and neuronal NOS, or eNOS and nNOS, respectively. Studies have shown that both isoforms are inactive at basal intracellular levels of $Ca^{2+}$, however, their activity increases with elevated $Ca^{2+}$, reaching half-maximal activity at about 300 nM. Thus, nNOS and eNOS are regulated by changes in intracellular $Ca^{2+}$ concentrations within the physiological range. In contrast, a third, inducible isoform of NOS ("iNOS"), which is up-regulated during inflammation by macrophages and/or neutrophils, contains CaM that is tightly bound, even at low resting levels of cytosolic $Ca^{2+}$, and is not sensitive to intracellular $Ca^{2+}$.

Once cNOS is activated by CaM it converts its substrate, L-arginine, to citrulline, releasing one molecule of NO. As a gaseous free radical with a half-life of about 5 sec, NO diffuses locally through membranes and organelles and acts on molecular targets at a distance up to about 200 μm. The low transient concentrations of NO from cNOS can activate soluble guanylyl cyclase ("sGC"), which catalyzes the synthesis of cyclic guanosine monophosphate ("cGMP"). The CaM/NO/cGMP signaling pathway is a rapid response cascade which can modulate peripheral and cardiac blood flow in response to normal physiologic demands, as well as to inflammation. This same pathway also modulates the release of cytokines, such as interleukin-1beta ("IL-1β") and growth factors such as basic fibroblast growth factor ("FGF-2") and vascular endothelial growth factor ("VEGF") which have pleiotropic effects on cells involved in tissue repair and maintenance.

Following an injury, e.g., a bone fracture, torn rotator cuff, sprain, strain or surgical incision, repair commences with an inflammatory stage during which the pro-inflammatory cytokine IL-1β is rapidly released. This, in turn, up-regulates iNOS, resulting in the production of large amounts of NO in the wound bed. Continued exposure to NO leads to the induction of cyclooxygenase-2 and increased synthesis of prostaglandins which also play a role in the inflammatory phase. While this process is a natural component of healing, when protracted, it can lead to increased pain and delayed or abnormal healing. In contrast, CaM/eNOS/NO signaling has been shown to attenuate levels of IL-1β and down-regulate iNOS. As tissue further responds to injury, the CaM/NO/cGMP cascade is activated in endothelial cells to stimulate angiogenesis, without which new tissue growth cannot be sustained. Evidence that non-thermal EMF can modulate this cascade is provided by several studies. An early study showed that the original BGS signal promoted the creation of tubular, vessel-like, structures from endothelial cells in culture in the presence of growth factors. Another study using the same BGS signal confirmed a seven-fold increase in endothelial cell tubularization in vitro. Quantification of angiogenic proteins demonstrated a five-fold increase in FGF-2, suggesting that the same BGS signal stimulates angiogenesis by increasing FGF-2 production. This same study also reported increased vascular in-growth more than two-fold when applied to an implanted Matrigel plug in mice, with a concomitant increase in FGF-2, similar to that observed in vitro. The BGS signal significantly increased neovascularization and wound repair in normal mice, and particularly in diabetic mice, through an endogenous increase in FGF-2, which could be eliminated by using a FGF-2 inhibitor.

Similarly, a pulse modulated radio frequency ("PRF") signal of the type used clinically for wound repair was reported to significantly accelerate vascular sprouting from an arterial loop transferred from the hind limb to the groin in a rat model. This study was extended to examine free flap survival on the newly produced vascular bed. Results showed 95% survival of PRF-treated flaps compared to 11% survival in the sham-treated flaps, suggesting a significant clinical application for PRF signals in reconstructive surgery.

In some embodiments, the proposed EMF transduction pathway relevant to tissue maintenance, repair and regeneration, begins with voltage-dependent $Ca^{2+}$ binding to CaM, which is favored when cytosolic $Ca^{2+}$ homeostasis is disrupted by chemical and/or physical insults at the cellular level. Ca/CaM binding produces activated CaM that binds to, and activates, cNOS, which catalyzes the synthesis of the signaling molecule NO from L-arginine. This pathway is shown in its simplest schematic form in FIG. 1.

As shown in FIG. 1, cNOS* represents activated constitutive nitric oxide synthase (cNOS), which catalyzes the production of NO from L-arginine. The term "sGC*" refers to activated guanylyl cyclase which catalyzes cGMP formation when NO signaling modulates the tissue repair pathway. "AC*" refers to activated adenylyl cyclase, which catalyzes cyclic adenosine monophosphate ("cAMP") when NO signaling modulates differentiation and survival. According to some embodiments, an EMF signal can be configured to accelerate cytosolic ion binding to a cytosolic buffer, such as $Ca^{2+}$ binding to CaM, because the rate constant for binding, $k_{on}$, is voltage-dependent and $k_{on}$ is much greater than the rate constant for unbinding, $k_{off}$, imparting rectifier-like properties to ion-buffer binding, such as $Ca^{2+}$ binding to CaM.

For example, EMF can accelerate the kinetics of $Ca^{2+}$ binding to CaM, the first step of a well characterized cascade that responds to chemical or physical insults. Ca/CaM binding is kinetically asymmetrical, i.e., the rate of binding exceeds the rate of dissociation by several orders of magnitude ($k_{on} \gg k_{off}$), driving the reaction in the forward direction. Ca/CaM binding has been well characterized, with the binding time constant reported to be in the range of $10^{-2}$-$10^{-3}$ sec. In contrast, release of $Ca^{2+}$ from CaM cannot occur until cNOS* has converted L-arginine to citrulline and NO, which takes the better part of a second. Subsequent reactions involving NO depend upon the cell/tissue state. For example, tissue repair requires a temporal sequence of inflammatory, anti-inflammatory, angiogenic and proliferative components. Endothelial cells orchestrate the production of FGF-2 and VEGF for angiogenesis. For each of these phases, early NO production by endothelial cells, leading to increased cGMP by these, as well as other NO targets, such as vascular smooth muscle, would be expected to be modulated by an EMF effect on sGC via Ca/CaM binding. In contrast, nerve or bone regeneration may require other pathways leading to differentiation during development and growth, and prevention of apoptosis, as in response to injury or neurodegenerative diseases. For these cases, early cAMP formation would be modulated by an EMF effect on sAC via Ca/CaM binding.

The substantial asymmetry of Ca/CaM binding kinetics provides a unique opportunity to configure EMF signals that selectively modulate $k_{on}$. In general, if $k_{on} \gg k_{off}$, and $k_{on}$ is voltage-dependent, according to the present invention, ion binding could be increased with an exogenous electric field signal having a carrier period or pulse duration that is significantly shorter than the mean lifetime of the bound ion. This applies to the CaM signaling pathway, causing it to exhibit rectifier-like properties, i.e., to yield a net increase in the population of bound $Ca^{2+}$ because the forward (binding) reaction is favored. The change in surface concentration, $\Delta\Gamma$, of $Ca^{2+}$ at CaM is equal to the net increase in the number of ions that exit the outer Helmholtz plane, penetrate the water dipole layer at the aqueous interface of the binding site, and become bound in the inner Helmoltz plane. For the general case of ion binding, evaluation of Ca/CaM binding impedance, $ZA(s)$, allows calculation of the efficacy of any given waveform in that pathway by evaluating the frequency range over which the forward binding reaction can be accelerated. Thus, binding current, $IA(t)$, is proportional to the change in surface charge (bound ion concentration) via $dq(t)/dt$, or, in the frequency domain, via $sqA(s)$. $IA(s)$ is, thus, given by:

$$I_A(s) = sq_A(s) = s\Gamma_o f(\Delta\Gamma(s)) \quad (1)$$

where s is the real-valued frequency variable of the Laplace transform. Taking the first term of the Taylor expansion of equation 1 gives:

$$I_A(s) = q_\Gamma s \Gamma_o \Delta\Gamma(s) \quad (2)$$

where $q\Gamma = \partial_q/\partial\Gamma$, a coefficient representing the dependence of surface charge on bound ion concentration. $\Delta\Gamma(s)$ is a function of the applied voltage waveform, $E(s)$, and, referring to the reaction scheme in FIG. 1, of the change in concentration of eNOS*, defined as $\Delta\Phi(s)$:

$$\Delta\Gamma(s) = k_{on}/\Gamma_o s[-\Delta\Gamma(s) + aE(s) + \Delta\Phi(s)] \quad (3)$$

where $F_o$ is the initial surface concentration of $Ca^{2+}$ (homeostasis), and $a = \partial\Gamma/\partial E$, representing the voltage dependence of $Ca^{2+}$ binding. Referring to the reaction scheme in FIG. 1, it may also be seen that eNOS* depends only upon $Ca^{2+}$ binding, i.e., $\Delta\Gamma(s)$. Thus:

$$\Delta\Phi(s) = v_\Phi / \Phi_o s [-\Delta\Phi(s) - \Delta\Gamma(s)] \quad (4)$$

where $v\Phi$ is the rate constant for Ca/CaM binding to eNOS and $\Phi_o$ is the initial concentration of eNOS* (homeostasis).

Using equations 2, 3 and 4, and for $k_{on} \gg v_\Phi$, ZA(s) may be written:

$$Z_A(s) = \frac{E(s)}{I_A(s)} = \frac{1}{q_\Gamma a}\left[\frac{1 + \Gamma_o s/k_{on}}{\Gamma_o s}\right] \quad (5)$$

Equation 5 describes the overall frequency response of the first binding step in a multistep ion binding process at an electrified interface, wherein the second step requires that the bound ion remain bound for a period of time significantly longer than the initial binding step. For this case, the first ion binding step is represented by an equivalent electrical impedance which is functionally equivalent to that of a series $R_A$-$C_A$ electric circuit, embedded in the overall dielectric properties of the target. $R_A$ is inversely proportional to the binding rate constant ($k_{on}$), and $C_A$ is directly proportional to bound ion concentration.

Some embodiments provide that an electromagnetic field, for which pulse duration or carrier period is less than about half of the bound ion lifetime can be configured to maximize current flow into the capacitance CA, which will increase the voltage, $E_b(s)$, where s is the LaPlace frequency, across CA. $E_b(s)$ is a measure of the increase in the surface concentration of the binding ion in the binding sites of the buffer, above that which occurs naturally in response to a given physiological state. The result is an increase in the rate of biochemical signaling in plant, animal and human repair, growth and maintenance pathways which results in the acceleration of the normal physiological response to chemical or physical stimuli. The following equation demonstrates the relation between the configured electromagnetic waveform, E(s) and $E_b(s)$.

$$E_b(s) = \frac{(1/sC_A)E(s)}{(R_A^2 + (1/sC_A)^2)^{1/2}} \quad (6)$$

Some embodiments also provide that a time-varying electromagnetic field for which pulse duration or carrier period is less than about half of the bound ion lifetime of $Ca^{2+}$ binding to CaM will maximize the current flow into the Ca/CaM binding pathway to accelerate the CaM-dependent signaling which plants, animals and humans utilize for tissue growth, repair and maintenance. In particular, a time-varying electromagnetic field may be configured to modulate CaM-dependent NO/cGMP signaling which accelerates; pain and edema relief, angiogenesis, hard and soft tissue repair, repair of ischemic tissue, prevention and repair of neurodegenerative diseases, nerve repair and regeneration, skeletal and cardiac muscle repair and regeneration, relief of muscle pain, relief of nerve pain, relief of angina, relief of degenerative joint disease pain, healing of degenerative joint disease, immunological response to disease, including cancer.

Other embodiments provide for an electromagnetic signal which accelerates the kinetics of $Ca^{2+}$ binding by maximizing non-thermal $E_b(s)$ at its CaM binding sites, consisting of a 1-10 msec pulse burst of 27.12 MHz radio frequency sinusoidal waves, repeating between about 1 and about 5 bursts/sec and inducing a peak electric field between about 1 and about 100 V/m, then coupling the configured waveform using a generating device such as ultra lightweight wire coils that are powered by a waveform configuration device such as miniaturized electronic circuitry which is programmed to apply the waveform at fixed or variable intervals, for example 1 minute every 10 minutes, 10 minutes every hour, or any other regimen found to be beneficial for a prescribed treatment.

Figure 2:
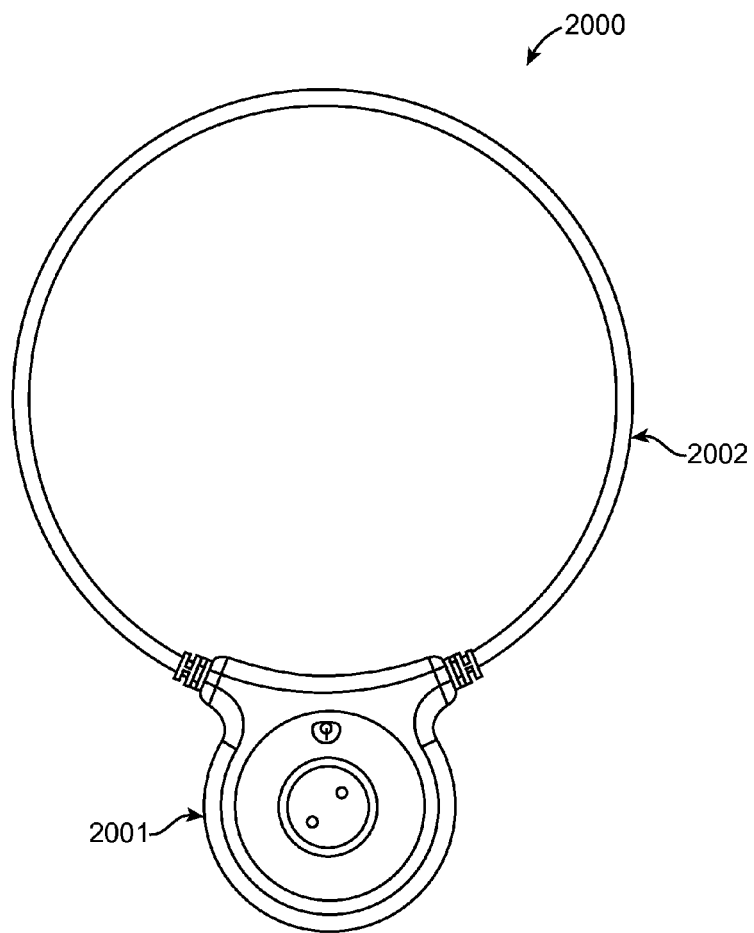
FIG. 2 illustrates a device for application of electromagnetic signals according to embodiments of the devices and methods described herein.

As an example of an EMF generating device, FIG. 2 illustrates a delivery apparatus with a control circuit or signal generator 2001 connected to an applicator 2002 such as an electrical coil 2002. The control circuit 2001 generates an electromagnetic signal that is sent through the applicator 2002 and delivered as an electromagnetic field. In some embodiments, the control circuit 2001 is constructed in a manner that given a target pathway within a target tissue, it is possible to choose waveform parameters that satisfy a frequency response of the target pathway within the target tissue. For some embodiments, control circuit 2001 applies mathematical models or results of such models that describe the dielectric properties of the kinetics of ion binding in biochemical pathways. For some embodiments, control circuit 2001 applies mathematical models or results of such models that modulate the internal regimens of the biochemical cascades involved in tissue repair and growth.

While devices such as those shown in FIG. 2, are generally used to provide post-operative treatment to promote healing, pain relief, etc., such devices have not been used for treatment of patients having metal implants or prosthetics. EMF devices generally are not approved by regulatory bodies for treatment of patients having metal implants because metal in the presence of an electromagnetic field can distort and interfere with the integrity, structure, behavior, and strength of the field. For example, a distorted field may not have the requisite strength or shape to target a treatment pathway (e.g. Ca/CaM). Or, a metal implant may absorb the electromagnetic field and generate unwanted heat in the treatment area and cause harm to the tissue surrounding the metal.

Figure 3:
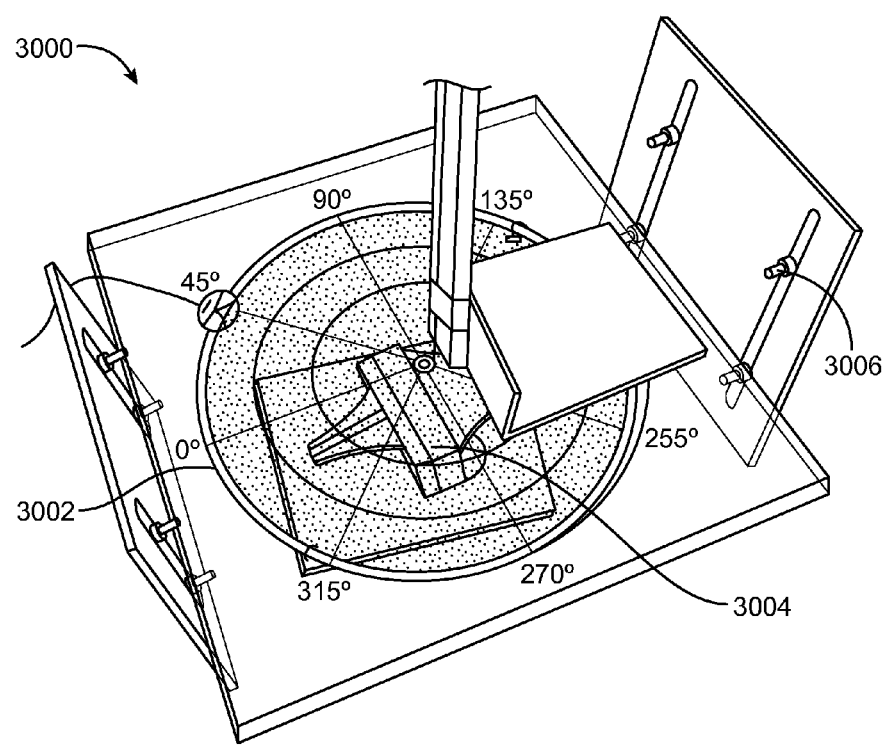
FIG. 3 illustrates a test jig used to test the electromagnetic field generated in the presence of metal-containing knee implants.

As an example of how metal-containing implants can interfere with electromagnetic field treatments, FIGS. 3-7 illustrate tests performed on two separate metal knee implants commonly used for knee replacement procedures. FIG. 3 shows a test jig 3000 constructed to mount an eight-inch EMF applicator 3002 from fixed distances above a metal implant 3004. The EMF applicator 3002 was fixed to a flat piece of plexi-glass. The interior of the applicator 3002 was marked in polar coordinates with concentric rings every one inch from the center marked every 45 degrees. A first set of baseline measurements with no implant present were measured at points on the interior (area on and within the circumference of the EMF applicator 3002). Measurements were then obtained at the same points in the interior of the applicator 3002 with each of the implants. A first set of measurements were taken with the coil in line with the highest point on an implant and a second set of measurements were taken at a half-an-inch above the highest point of the implant. The table shown in FIG. 32 shows the results of the measurements for the baseline, BioMet knee implant, and DePuy knee implant.

The results (shown in FIG. 32) indicate that for both the BioMet and DePuy knee implants, the metal implants interfered with the structure of the electromagnetic field. For example, the strength of the EMF at zero degrees and zero inches above the highest point of the BioMet knee implant showed a 15.7% reduction in strength. Similarly, at the same location, the DePuy knee implant reduced the EMF by 19.1%. In some cases, the interference reduced EMF strength by over 50%.

Figure 4:
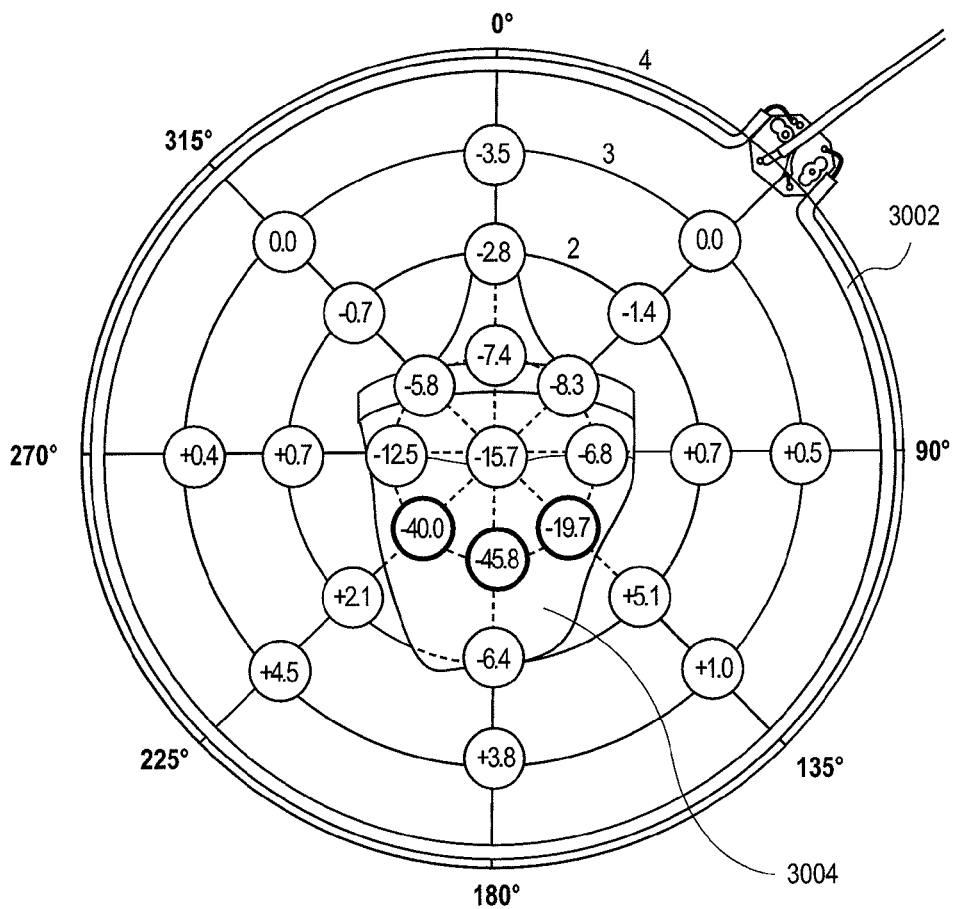
FIG. 4 illustrates the percentage change in the electromagnetic field generated at the highest point of a BioMet knee implant.
Figure 5:
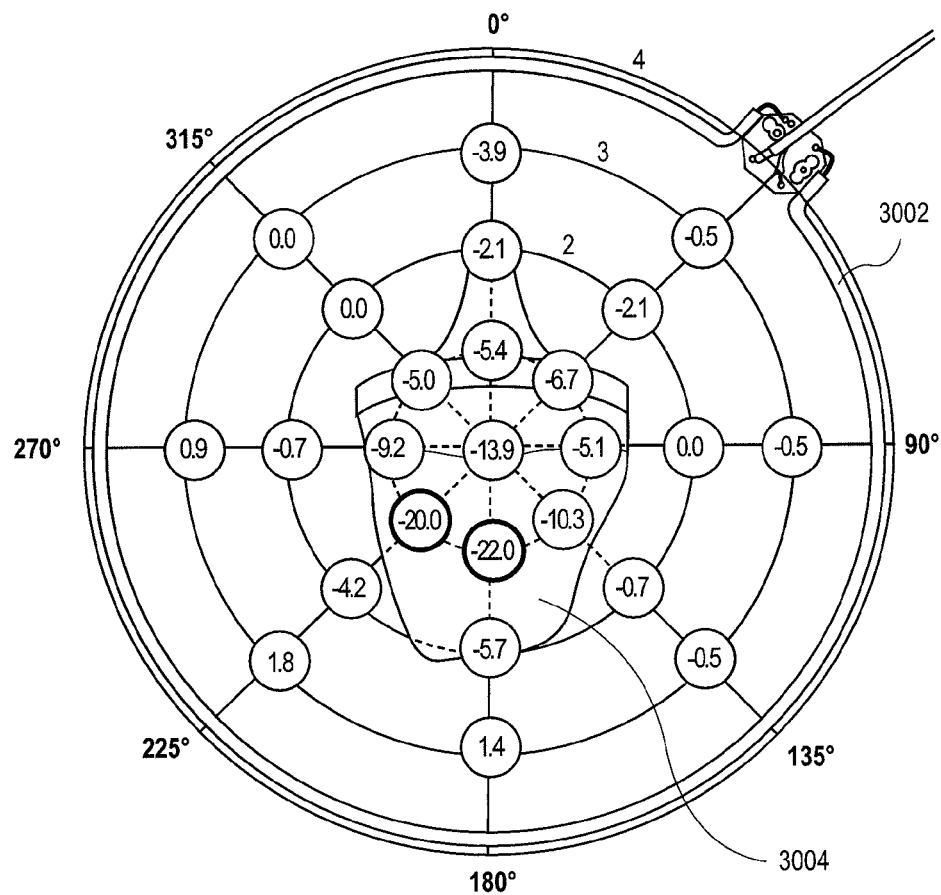
FIG. 5 illustrates the percentage change in the electromagnetic field generated at half-an-inch above the highest point of the BioMet knee implant.
Figure 6:
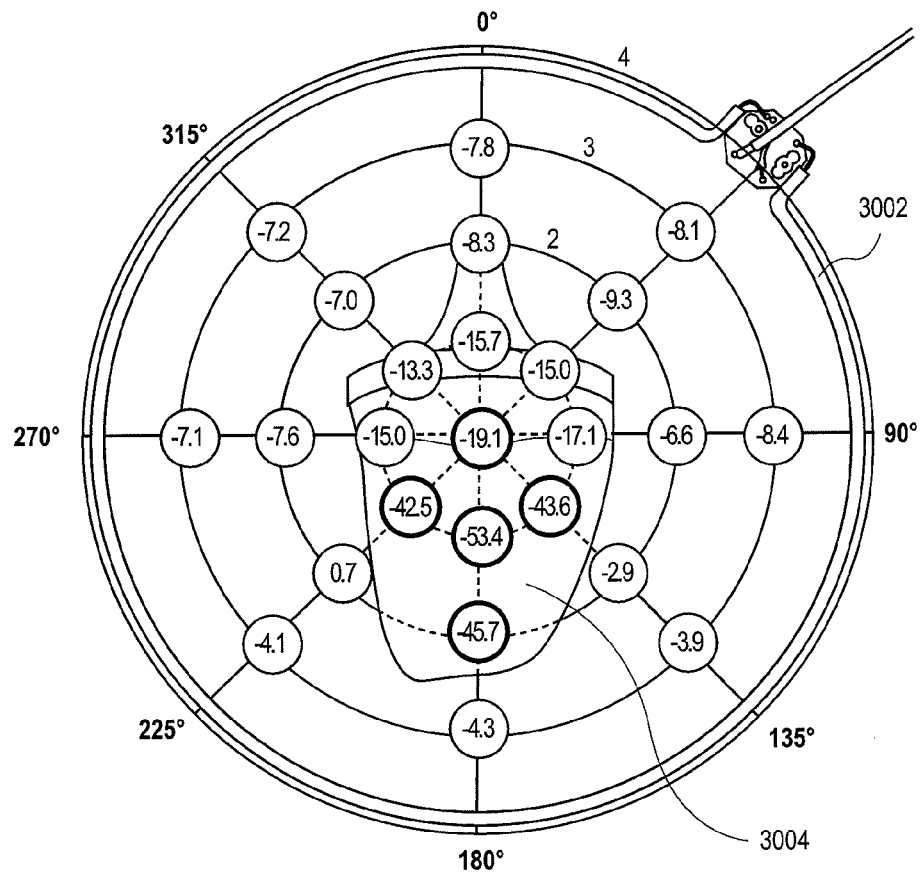
FIG. 6 illustrates the percentage change in the electromagnetic field generated at the highest point of a DePuy knee implant.
Figure 7:
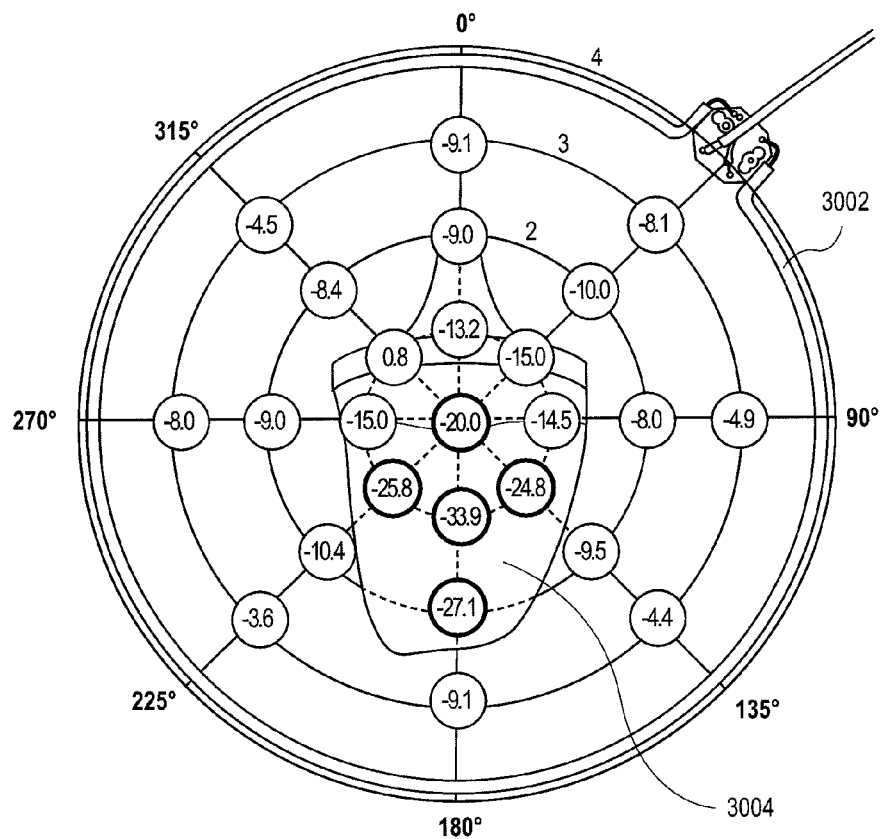
FIG. 7 illustrates the percentage change in the electromagnetic field generated at half-an-inch above the highest point of the DePuy knee implant.

FIGS. 4 and 5 illustrate the EMF applicator 3002 positioned around the BioMet knee implant in the test jig. The measured percentage change in the EMF field compared to baseline measurements are shown at the measured heights and degrees around the implant within the interior of the applicator 3002. FIG. 4 shows the percentage change in the EMF field with the applicator coil in line with the highest point on the implant. FIG. 5 shoes the percentage change in the EMF field with the applicator coil half-an-inch above the highest point of the implant. FIGS. 6 and 7 illustrate the same for the DePuy knee implant. Generally, for all measurements, the greatest percentage change in EMF field strength occurred in close proximity to the metal implant. For example, in FIG. 6, the greatest percentage changes (42.5%, 53.4%, 43.6%, 45.7%, and 19.1%) are clustered near the center of the interior around the DePuy implant. On the other hand, the lower percentage changes to the EMF are located further out from the implants.

These comparative tests show that in order to provide EMF treatment to target locations near metal-containing prosthetics or implants, EMF delivery devices must be calibrated to account for the effects of metal on the generated field. To address this need, embodiments described herein provide devices and methods calibrated for such use.

Figure 8:
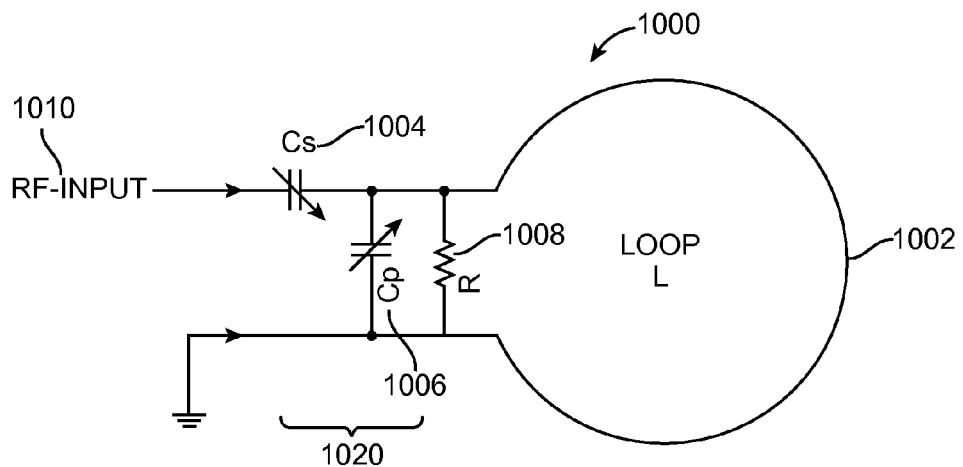
FIG. 8 illustrates schematically a control circuit and an applicator according to some embodiments described herein.

FIG. 8 schematically illustrates an EMF delivery device that can be calibrated for EMF treatment near a metal prosthetic. In some embodiments, the electromagnetic device 1000 of FIG. 8 has a control circuit 1020 and an applicator 1002 configured to provide a calibrated EMF field to a target treatment location. The control circuit 1020 is configured to generate an electromagnetic signal, which in some variations induces a pulsed electromagnetic field in the radiofrequency range ("RF") 1010. The control circuit 1020 can include, among other things, a resistor 1008, a parallel capacitor 1006, a series capacitor 1004, and other circuitry components. The electromagnetic signal generated by the control circuit is sent through the applicator 1002, which is configured to transmit and generate an electromagnetic field. In some cases, the control circuit is configured to provide an electromagnetic signal to the applicator to induce an electric field of peak amplitude between about 1 µV/m and about 100 V/m in the target tissue and a peak induced magnetic field between about 1 µT and about 0.1 T, wherein the signal generated by the control circuit comprises a burst of waveforms having a burst duration of greater than 65 µsec and a burst repetition rate of about 0.01 to about 1000 bursts per second.

Figure 9:
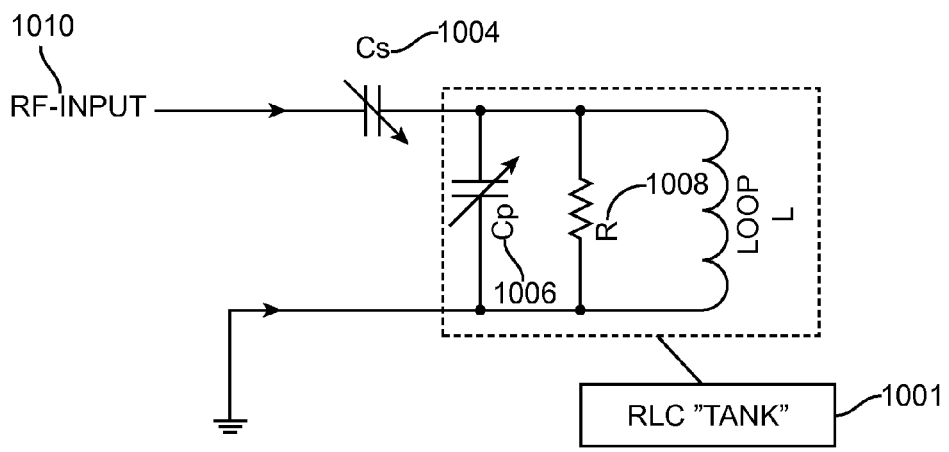
FIG. 9 illustrates schematically a control circuit, an applicator, and a RLC Tank according to some embodiments described herein.

The applicator 1002 may be a loop with a generally circular shape such as an oval, bent oval, or circle. The applicator 1002 may be made from a flexible metal wire loop or a metal coil. In further variations, the electrical coil is a circular wire applicator with a diameter that allows encircling of a target location such as a subject's knee or shoulder. In some embodiments, the diameter is between approximately 6-8 inches. In other embodiments, the diameter is between 2-20 inches. In general, the size of the coil may be fixed or adjustable and the circuit control/signal generator may be matched to the material and the size of the applicator to provide the desired treatment. Additionally, in some variations, as shown in FIG. 9, the parallel capacitor 1006, resistor 1008, and applicator 1002 of the device 1000 may be referred to collectively as the "RLC Tank" or "Tank".

In operation, the treatment device 1000 can be calibrated for use near a metal-containing implant or prosthesis. In some variations, the calibration process calibrates the device. As used herein, the term "calibrate" or "calibrating" may include calibrating a device, component(s) of a device (e.g. applicator), or the electromagnetic field generated from a device such that it has substantially no inductive reactance and substantially no capacitance reactance when operated in the presence of metal. Although a calibrated device may be configured to completely eliminate or reduce the inductive and capacitance component of reactance when operated in proximity to metal, generally a range of inductive and capacitive reactance can be present without significantly affecting the EMF output. A calibrated device may have a substantially purely resistive reactance. However, substantially purely resistive reactance also does not require a completely resistive reactance. For example, "substantially" may refer to >85%, >90%, >91%, >92%, >95%, >93%, >94%, >95%, >96%, >97%, >98%, >99%, or more, up to all (100%). "Substantially no" may refer to <15%, <10%, <9%, <8%, less than 7%, less than 6%, less than 5%, less than 4%, less than 3%, less than 2%, less than 1%, less than 0.1%, etc., up to 0%.

A calibrated device as described herein may have substantially no inductive and capacitive reactance when operated in proximity to metal but have either or both components when not operated in the presence of metal. In other words, the calibrated device may have different reactance when operated near metal versus when operated outside the presence of metal. Alternatively, the device may be calibrated to have no inductive or capacitance reactance regardless of proximity to metal in the treatment location. In further embodiments, the calibrated device can effectively provide therapeutic EMF in either the presence or absence of metal. For example, the calibrated device may have substantially no inductive or capacitive reactance when operated near a metal prosthetic but have some inductive or capacitive reactance when operated otherwise; however, under both situations, the device is calibrated to deliver EMF for therapeutic treatment.

Figure 10:
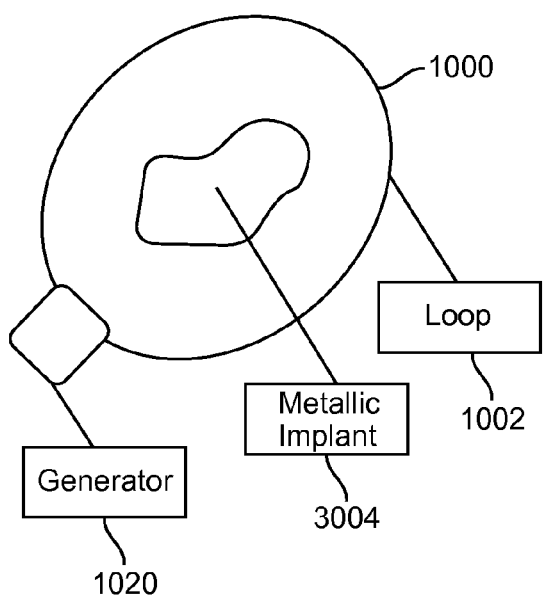
FIG. 10 illustrates schematically an electromagnetic treatment device near a metal-containing prosthetic.

As shown in FIG. 10, to calibrate the electromagnetic treatment device 1000, the treatment device 1000 is placed in proximity to, near, around, or adjacent a metal-containing material. The control circuit 1020 is activated to transmit an electromagnetic signal to the applicator 1002. The applicator 1002 generates an electromagnetic field. While the device 1000 is active, the reactance of the device 1000 will generally comprise either or both inductive and capacitance components while in proximity to the metal. It is believed that having either an inductive or capacitance reactance contributes to the interference of the electromagnetic field by the metal. For example, the inductance of the applicator 1002 is generally a function of the magnetic permeability and the physical geometry of the applicator loop. Because metals tend to have a higher permeability, metals in implants will effectively increase the inductance of the applicator loop. This increase in inductance alters the electromagnetic field that would normally be generated by the applicator in the absence of metal.

Figure 11:
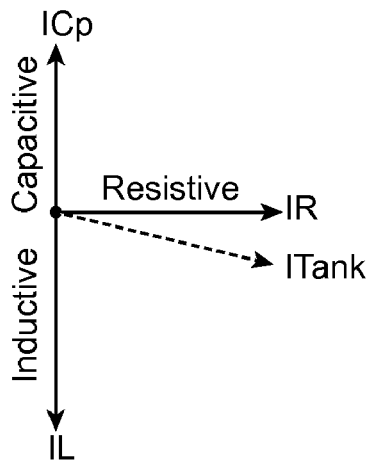
FIG. 11 illustrates the capacitive and inductive components of an applicator's reactance according to some embodiments described.
Figure 12:
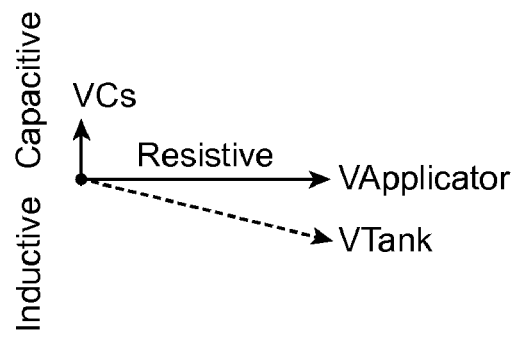
FIG. 12 illustrates an example of a calibrated applicator according to some embodiments.

To account for this interference, device 1000 can be adjusted to balance any inductive or capacitive components of the reactance that may arise. Specifically, in some embodiments, the series capacitor 1004 and parallel capacitor 1006 can be adjusted to substantially reduce or eliminate inductive or capacitive components. FIGS. 11 and 12 provide an example of calibrating a device 1000 having an inductive reactance in the presence of metal. As shown in FIG. 11, $I_R$ represents the resistive axis dividing the region between capacitive and inductive reactance. $I_{C_P}$ represents the value of the capacitance reactance. $I_L$ represents the value of the inductive reactance. $I_{Tank}$ represents the reactance of the RLC Tank 1001 of the device 1000. As shown, the device 1000 has a slightly inductive reactance. The $I_{Tank}$ is below the purely resistive axis in the inductive $I_L$ region. To correct this, the series capacitance is adjusted to balance out the inductive reactance. FIG. 12 illustrates that the series capacitor is adjusted to offset the inductance of the Tank and yield a reactance for the applicator along the resistive axis. The resulting reactance is substantially purely resistive.

Although the example in FIGS. 11 and 12 illustrate the calibrating or calibrating of an inductive device, the method of calibrating can be applied to a device having only a capacitance reactance (i.e. no inductive component) or to one with a combination of inductive and capacitance components. Moreover, in some embodiments, it is advantageous to calibrate the electromagnetic treatment device by utilizing a reference metal implant that is located relative to the applicator loop as an implant would be located for actual treatment. However, alternatively, any reference metal material and any location may be used for the calibrating process such that the calibration substantially reduces or eliminates the inductive and capacitive reactance.

Additionally, in some variations, the treatment devices may be pre-calibrated with a reference metal prior to treatment. For example, the treatment devices may be pre-calibrated for use with a specific metal implant such as the BioMet knee implant prior to treating a patient having a BioMet knee implant. In other variations, the device may be calibrated using the patient's own metal implant for the calibrating process prior to administering treatment. In further embodiments, the treatment devices may be calibrated or calibrated for a first metal implant and then subsequently calibrated for another metal implant.

Additionally, the EMF delivery devices provided can also include a tuning circuit to calibrate the applicator of the EMF delivery devices. The tuning circuit may be connected to the applicator and include a series capacitor and a parallel capacitor. Additionally, the tuning circuit may be configured to substantially eliminate or reduce any inductive or capacitance component of the applicator when the applicator generates an electromagnetic field near, around, adjacent, or in proximity to metal material. In calibrating the EMF delivery device, the tuning circuit may also substantially eliminate the inductive and capacitive components such that the applicator is primarily resistive. In some variations, the tuning circuit changes the reactance of the applicator by adjusting either or both the series capacitor and the parallel capacitor. In some variations the tuning circuit has an impedance value of about 50 ohms at 27.120 MHz.

Advantageously, in some variations, the calibrating process described herein can calibrate the device for use near a metal prosthetic without changing the power supply requirements of the device. For example, if 6-volts are required to run an EMF device for a treatment regimen outside the presence of metal, the calibration processes described herein can calibrate the device to provide the same treatment in the presence of metal without changing the 6-volt power requirement of the device. This allows, in some cases, the subject to use the same device for treating locations with and without metal prosthetics without having to change the power input of the device.

Once a device has been calibrated for use near a metal-containing implant or prosthesis, the device can provide beneficial post-operative EMF treatment to patients with metal prosthetics. For example, patients undergoing joint replacement procedures often receive metal-containing implants such as knee or shoulder implants. Following the surgical procedure, the injured soft tissue around and at the surgical site is often in close proximity to the metal implant. As such, EMF treatment has not been provided to this areas for the reasons discussed above. However, some embodiments herein deliver EMF treatment near, adjacent, or in proximity to the metal implant by placing a calibrated applicator of an electromagnetic treatment device in proximity to the tissue around the metal-containing prosthesis. Once in place, the delivery device can generate an electromagnetic field from the calibrated applicator such that the metal-containing prosthetic will not interfere with the delivered field. In some cases, the calibrated applicator achieves this by changing the reactance of the applicator such that the reactance is substantially purely resistive in the presence of the metal-containing prosthesis.

Advantageously, the calibrated devices described can provide immediate treatment following a surgical procedure. For example, studies have shown that treatment within the first 90 days following surgery can greatly promote healing in patients undergoing implant procedures. Because the devices provided herein can be used in the presence of a metal prosthesis, treatment can be provided immediately after the operative event and can continue for up to 90 days or more.

For the treatment itself, the calibrated devices can deliver induced time-varying electric fields (e.g PEMF) configured to affect the treatment location by targeting specific cellular/molecular pathways in the target tissues allowing these tissues to react in a physiologically meaningful manner. For example, a waveform may be configured within a prescribed set of parameters so that a particular pathway, such as CaM-dependent NO synthesis within the neurological tissue target, is modulated specifically. Both the applied waveform and the dosing or treatment regimen applied may be configured so that at least this pathway is targeted specifically and effectively. Furthermore, the stimulation protocol and dosing regimen may be configured so that the treatment delivery device may be portable/wearable, lightweight, require low power, and does not interfere with medical or body support such as wound dressings, orthopedic and other surgical fixation devices, and surgical interventions.

In some embodiments, a method of treating a subject includes applying the one or more (or a range of) waveforms that are needed to target the appropriate pathways in the target tissue. This determination may be made through calculation of mathematical models such as those described in U.S. Patent Publication No. 2011-0112352 filed Jun. 21, 2010 as U.S. patent application Ser. No. 12/819,956 (herein incorporated by reference) to determine the dosing regimen appropriate for modulating a molecular pathway (e.g. Ca/CaM pathway).

For example, as discussed above, it is believed that pathways involved in the maintenance and repair of tissue include the Ca/CaM pathway. To modulate this pathway, in some variations, the electromagnetic fields applied are configured to comprise bursts of at least one of sinusoidal, rectangular, chaotic or random wave shapes; burst duration less than about 100 msec, with frequency content less than about 100 MHz at 1 to 100 bursts per second. In other variations, the electromagnetic fields have a 1 to about a 50 msec burst of radio frequency sinusoidal waves in the range of about 1 to about 100 MHz, incorporating radio frequencies in the industrial, scientific, and medical band (ISM), for example 27.12 MHz, 6.78 MHz, or 40.68 MHz, repeating between about 0.1 to about 10 bursts/sec, with an induced amplitude of 0.001 G to 1 G. In further variations, an electromagnetic field can be applied that consists of a 2 msec burst of 27.12 MHz sinusoidal waves repeating at 2 Hz. In additional embodiments, an applied field can consist of a sinusoidal waveform of 27.12 MHz pulse-modulated with 4 msec bursts having amplitude of 0.001 G to 1 G, and repeating at 2 Hz. In additional embodiments, electromagnetic fields applied are configured to have a frequency content in a range of about 0.01 Hz to about 10,000 MHz having burst duration from about 0.01 to about 100 msec, and having a burst repetition rate from about 0.01 to about 1000 bursts/second.

Alternatively, the carrier signal frequency may be below 1 MHz, such as 100,000 Hz, 10,000 Hz, 100 Hz or 1 Hz. In such variations, the lower carrier signal frequency requires longer burst duration, e.g. 500 msec for 100 Hz carrier frequency, and higher amplitude of between about 0.1 G and 100 G.

Electromagnetic signals can be applied manually or automatically through application devices to provide a range of electromagnetic fields, treatment ranges and doses. For example, treatment can be applied for 15 minutes, 30 minutes, 60 minutes, etc. as needed for treatment. Electromagnetic signals can also be applied for repeated durations such as for 15 minutes every 2 hours. Treatment duration can also span minutes, days, weeks, etc. Although any amount of time for treatment can be provided depending on the needs of the patient, in some embodiments, the electromagnetic field is applied to the target location for twenty minutes every four hours. In other embodiments, the electromagnetic field is applied for five minutes every twenty minutes. In further embodiments, the electromagnetic field is applied for fifteen minutes every hour and forty-five minutes.

Furthermore, treatment can be provided for a therapeutic period of time. As used herein, the term therapeutic period is not limiting to any specific treatment regimen, but rather describes at least the total treatment period and treatment period per each treatment cycle. For example, a field may be applied for 15 minutes every 2 hours continuously until levels of tissue edema or pain decrease to acceptable levels. The therapeutic period would include at least the treatment interval, any inter-treatment interval, and the total treatment duration.

The treatment devices can also provide a time varying magnetic field (for example, peak=0.001 G to 100 G, Average=$10^{-6}$ G to $10^{-2}$ G) to induce a time varying electric field (for example average=0.1V/m to 100V/m) in the tissue target. Moreover, each signal burst envelope may be a random function providing a means to accommodate different electromagnetic characteristics of target tissue. Similarly, the number of treatments and the dose regime may vary depending on the progress of the target location.

In addition to the above, other embodiments described provide for easy-to-wear, adjustable, and durable EMF delivery devices that can be worn without affecting the effectiveness of the EMF treatment. Oftentimes, patients recovering from surgery have reduced mobility which may require patients to stay in certain positions for prolonged periods of time. Furthermore, as recovery progresses patients may undergo physical therapy that requires repetitive movement to regain body function. In such cases, use of EMF delivery devices has often been difficult because the applicators of devices can be bent, deformed, or broken when patients try to use the treatment devices while confined to certain positions or while moving. Once the applicator is deformed or broken, the treatment device no longer reliably provides the required electromagnetic field to the target location.

To address this challenge, described herein are embodiments of EMF delivery devices that can be adjusted to be worn or placed near a target treatment location such as an operation site while accommodating the patient's need for flexibility and comfort. Moreover, other embodiments also provide for wearable EMF delivery devices with support members to maintain the integrity of the delivered electromagnetic fields during use.

FIGS. 13-32 illustrate examples of a wearable and adjustable electromagnetic treatment device designed to maintain the integrity of the delivered EMF. As shown, the device 100 generally has an EMF applicator assembly 300 (see FIG. 20) having a control circuit 304 and an applicator 302. The applicator may be in the shape of a loop that is made from a flexible metal wire or coil. In some variations the coil or loop is between about 4 inches to about 11 inches. Generally, the device 100 has a stiffening or supporting member 102 that maintains the shape of the applicator loop and, thereby, maintains the integrity of the generated electromagnetic field.

Figure 13:
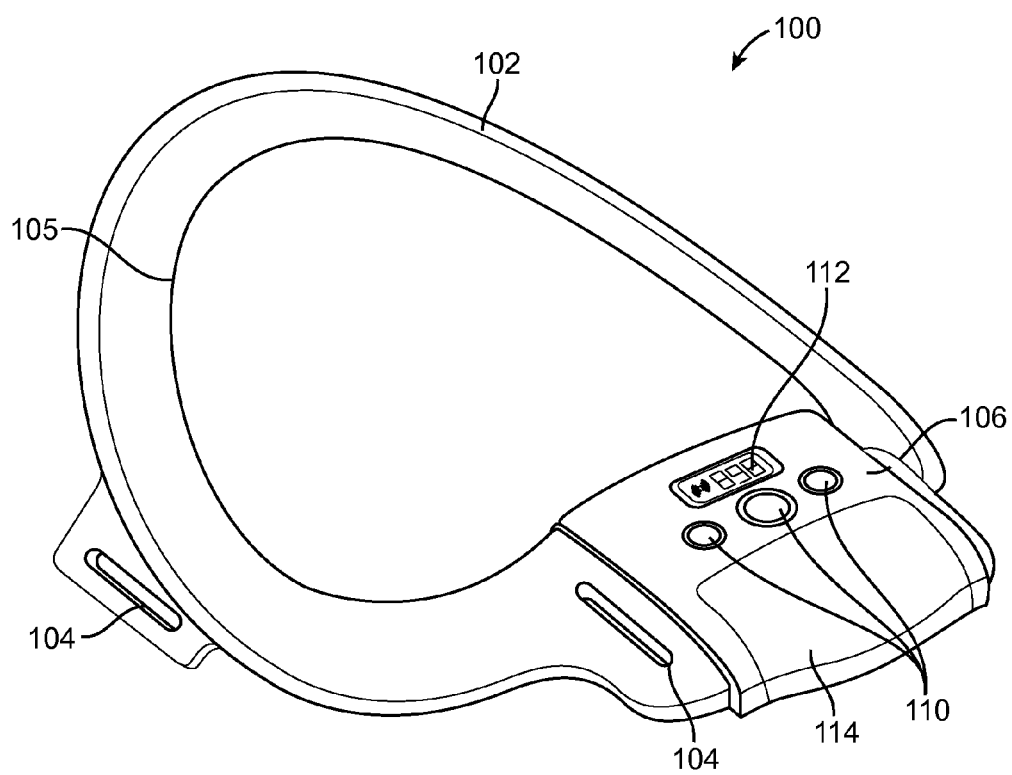
FIG. 13 illustrates a top view of a completed assembly of an electromagnetic treatment device described herein
Figure 14:
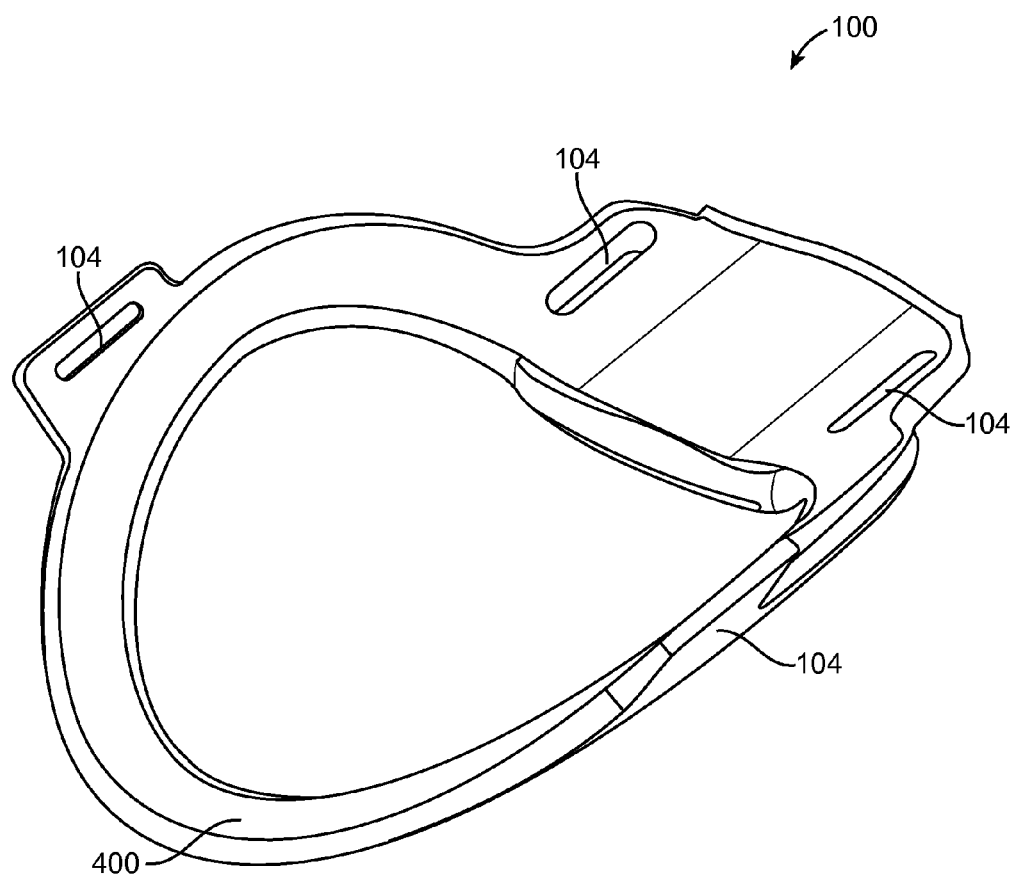
FIG. 14 illustrates a bottom view of a completed assembly of an electromagnetic treatment device described.

FIG. 13 shows a top view of one embodiment of the EMF device 100. The EMF treatment device 100 has an EMF applicator assembly 300 (not shown in FIG. 13) that is placed within the stiffening member 102 and housing of the device 100. In some variations, the stiffening member 102 includes strap attaching elements 104 that allow for adjustable straps to be releasably attached to the device 100. Additionally, the device 100 can include a power source such as a replaceable battery pack 114 and user display screen 112. In some variations, the user display also includes user interface components such as buttons for entering preferences and toggling between options. FIG. 14 provides a bottom view of the same device 100 in FIG. 13. In some embodiments, the device 100 may also include a bottom cover 400.

Figure 15:
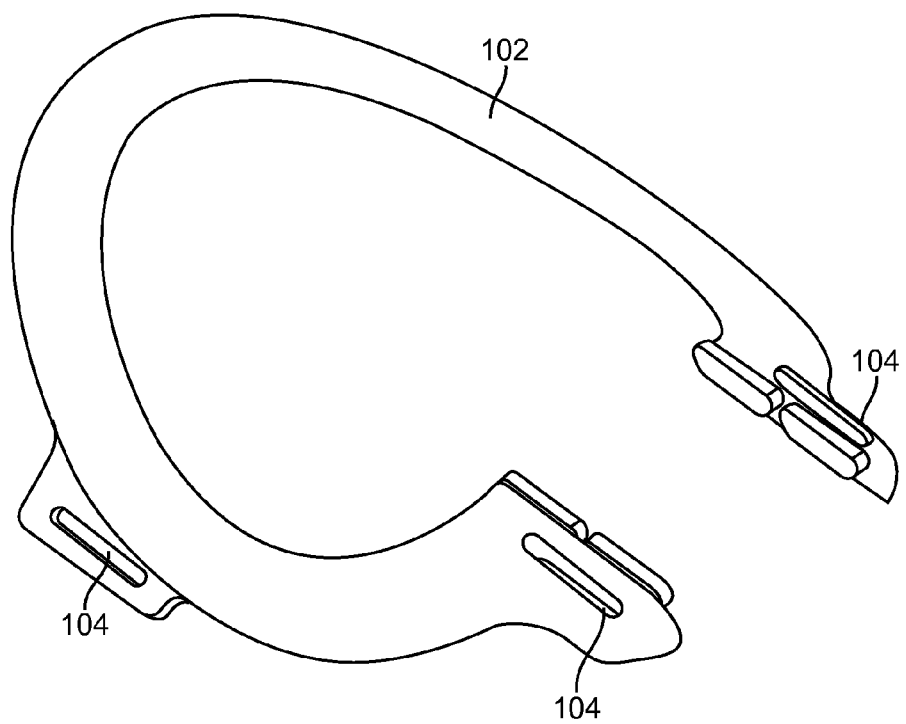
FIG. 15 shows a support or stiffening member of an electromagnetic treatment device.

To resiliently maintain the shape of an applicator and, in particular, the flexible metal applicator loop, a stiffening or support member 102 can be used to prevent bending and breaking of the applicator. For example, FIG. 15 shows a stiffening member 102 having a generally rounded shape for accommodating the rounded shape of an applicator coil. Although FIG. 15 provides a bent oval shape, any support member 102 for maintaining the shape of the applicator loop may be used depending on the shape of the applicator loop. The stiffening member can include a groove or a receiving indentation 122 along a surface of the stiffening member to accommodate placement of the applicator loop in the stiffening member (see FIG. 17). In some embodiments where the applicator loop is a flexible metal wire or coil, the stiffening member 102 may include a groove 122 on a bottom surface of the stiffening member that is sufficiently deep enough for the applicator loop to rest completely in the groove 122. In other variations, the applicator loop may partially reside in the receiving indentation or groove 122.

In some embodiments, the stiffening member is made of a molded foam material with sufficient resistance to deformation and bending to resiliently maintain the shape of the applicator. The molded foam material may be a polyolefin or an ethylene-vinyl-acetate ("EVA") foam, or foam made from a combination of EVA and polyolefin. Moreover, any variety of foams suitable for maintaining the shape of the applicator can be used. In other embodiments, the stiffening member may be made from a plastic that is suitable for providing structural support to the applicator. In further variations, the stiffening member can have a durometer of 70 asker C, density of 400 kg/m$^3$, tensile strength of 38 Kg/cm$^2$, tear strength of 22 kg/cm$^2$, and an elongation of 250%.

Additionally, the stiffening member 102 may have an enclosed or open structure. For example, in FIG. 15, the stiffening member 102 provides for a gap between the ends of the member to accommodate additional components of device 100. In other embodiments, the stiffening member may be completely enclosed and attached to circuitry through additional electrical connections. Where the stiffening member has a gap for additional components, the open portion may include connecting mechanisms to couple the stiffening member to other components. For example, the open portion may include a locking mechanism such as one with mating members, an interference fit, etc. designed to couple to a corresponding lock element. FIG. 15 shows a locking mechanism with protruding members 116 designed to releasably secure the stiffening member 102 to a housing top 106.

Figure 16:
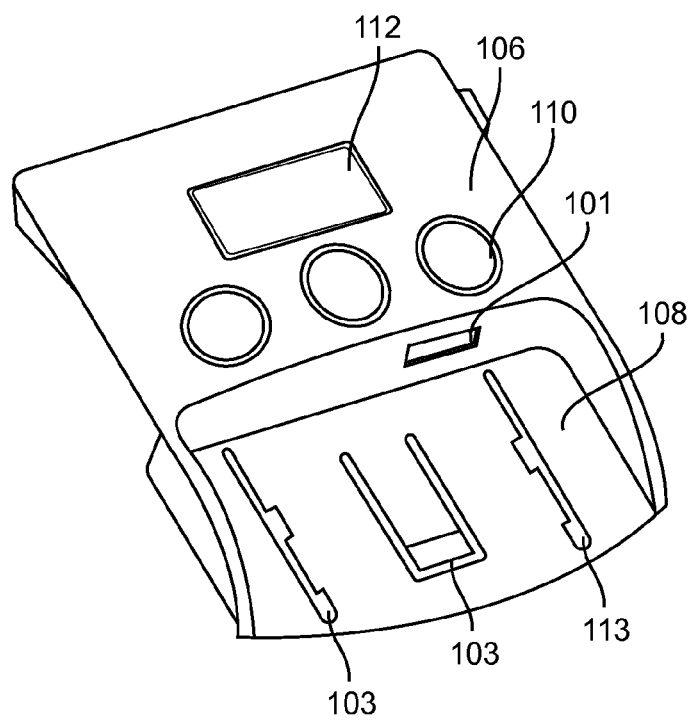
FIG. 16 illustrates a housing top of an electromagnetic treatment device.

Housing top 106, shown in FIG. 16, may include a user interface display screen 112, buttons 110, and a section 108 for receiving a power supply source such as a battery pack. Although shown with these features, the housing top may include additional or fewer subcomponents. In FIG. 16, the housing top 106 has a receiving section 108 for releasably attaching a battery pack. The battery pack may be replaceable or rechargeable, which would require removal from the housing top 106 once charge is depleted. The receiving section 108 may also include a locking mechanism 103 for releasably securing the power source supply to the housing top 106. In some embodiments, the receiving section 108 includes a connection port 101 to accommodate electrical connections between the power supply and other components of device 100.

Figure 17:
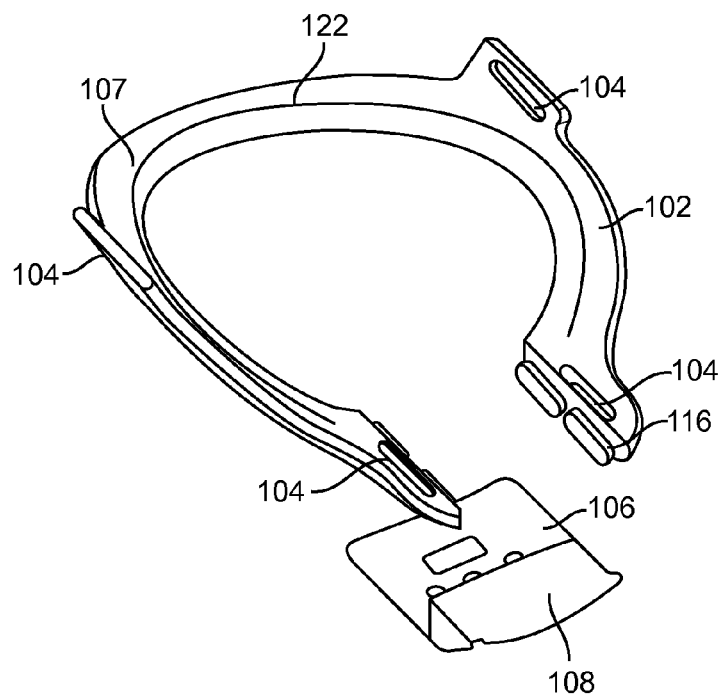
FIG. 17 illustrates the attachment of the housing top to the stiffening member of an electromagnetic treatment device.
Figure 18:
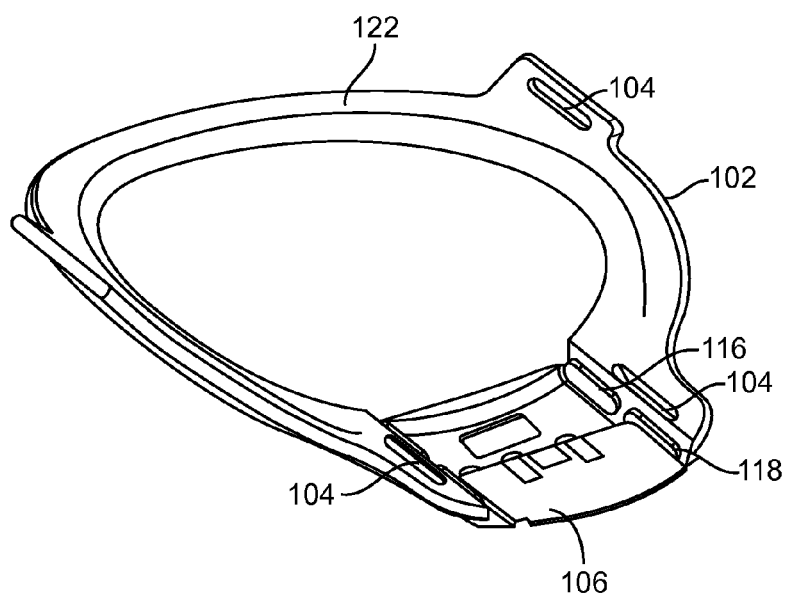
FIG. 18 illustrates the housing top attached to the stiffening member of an electromagnetic treatment device.
Figure 19A:
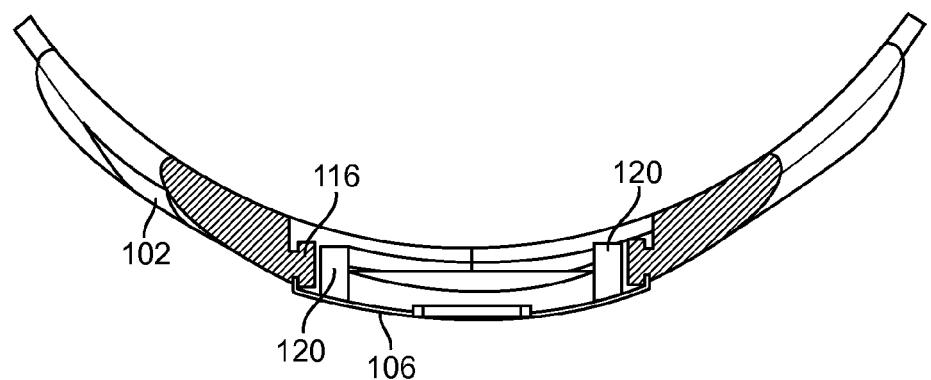
FIGS. 19A and 19B illustrate a side view of the attachment of the housing top to the stiffening member.
Figure 19B:
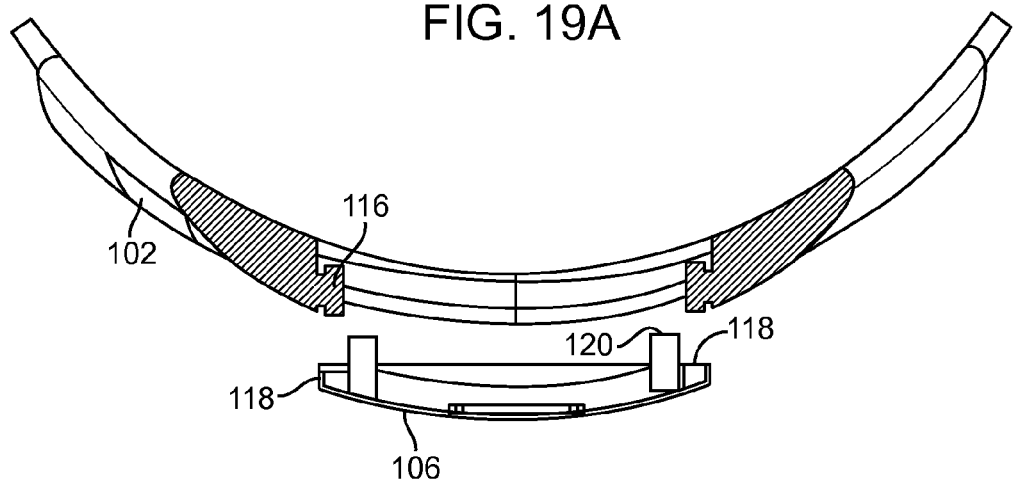

FIGS. 17 and 18 illustrate the attachment of the housing top 106 to the stiffening member 102. In the embodiment shown, the stiffening member 102 has a groove 122 for receiving an applicator loop on a bottom surface 107. The groove 122 extends along a circumference of the stiffening member from end to end. At the open portion of the stiffening member 102, the housing top 106 is configured to couple to the locking mechanism 116 of the stiffening member 102. The housing top 106 can include mating locking components 118 to couple the housing top 106 to the stiffening member 102. FIGS. 19A and 19B provide a side view of the housing top 106 attaching to the stiffening member 102. In some cases, the housing top 106 may include additional locking features 120 for attachment to other device components.

Figure 20A:
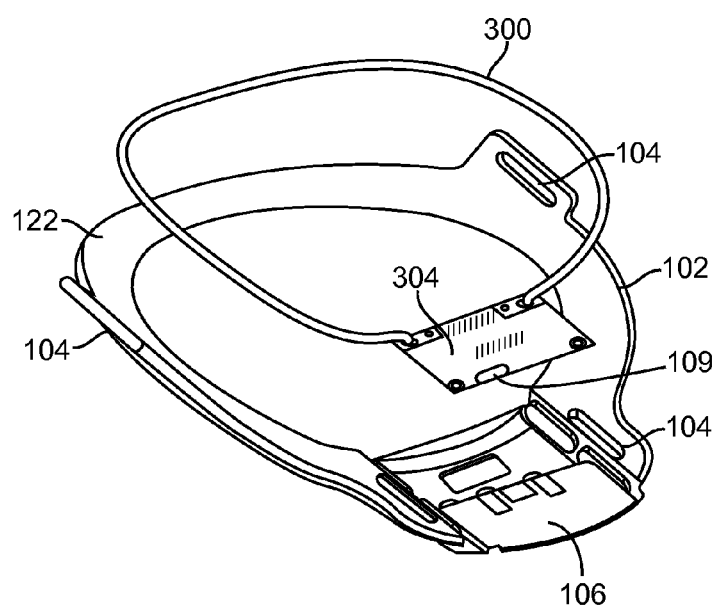
FIGS. 20A and 20B illustrate the placement and attachment of the EMF applicator assembly to the stiffening member and housing top.
Figure 20B:
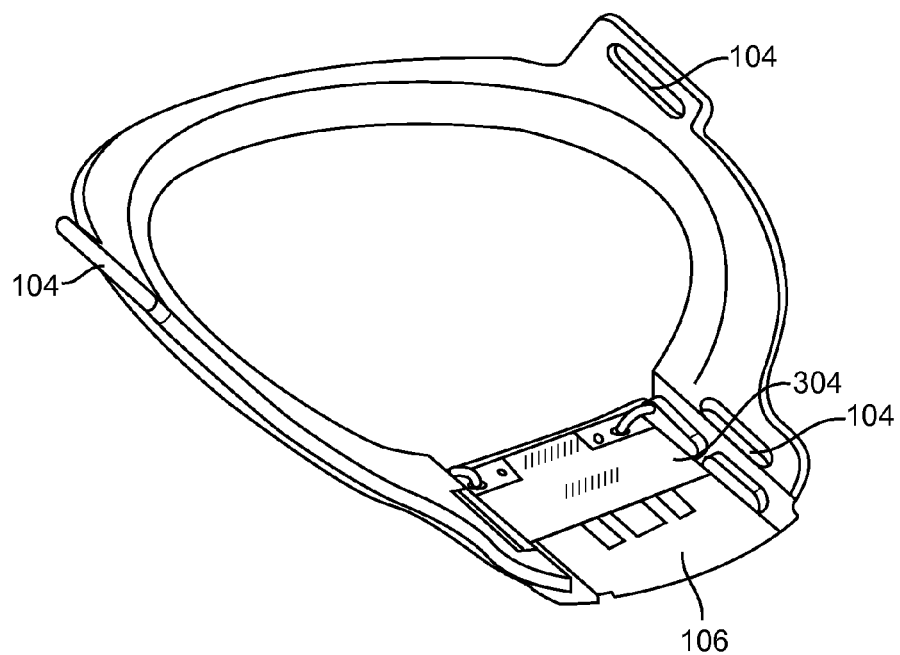

FIGS. 20A and 20B show the placement of the EMF applicator assembly 300 into the stiffening member 102 and housing top 106. The EMF applicator assembly 300 may include an applicator loop made from a flexible metal coil 302. Additionally, the assembly 300 may have a circuit board 304 with a control circuit or tuning circuit programmed to deliver an electromagnetic signal to the applicator loop 302. The circuit board 304 may also have circuitry designed to calibrate the applicator for use in proximity to a metal-containing prosthesis. Additionally, the circuit board 304 can include electrical connections 109 to electrically and physically connect to another device component such as a power source.

Figure 21A:
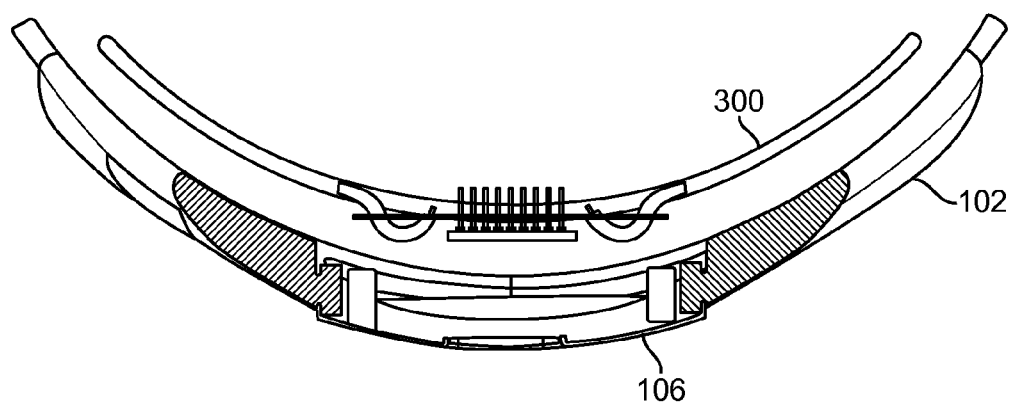
FIGS. 21A and 21B illustrate a side view of the attachment of the EMF applicator assembly to the stiffening member and housing top.
Figure 21B:
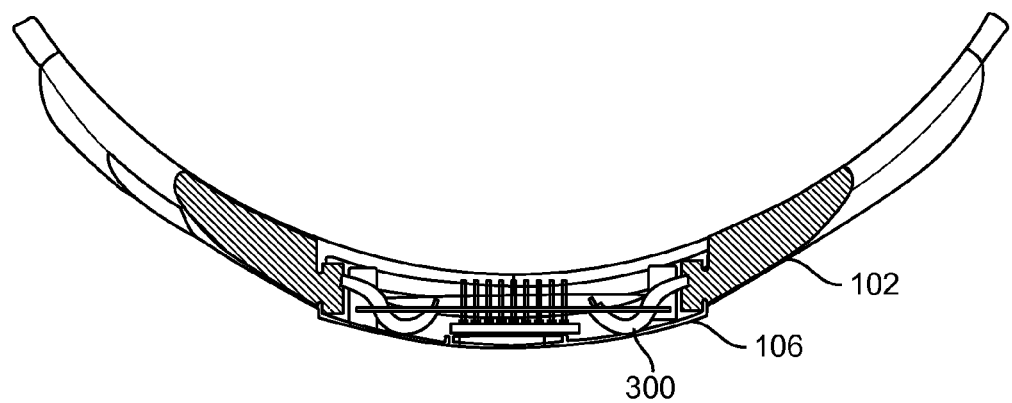

To couple the EMF applicator assembly 300 to the stiffening member 102, the applicator loop 302 is placed into the groove 122 of the stiffening member 102. The circuit board 304 is placed into the housing top 106. FIGS. 21A and 21B show a side view of the EMF applicator assembly 300 being placed into the stiffening member 102 and the housing top 106.

Figure 22:
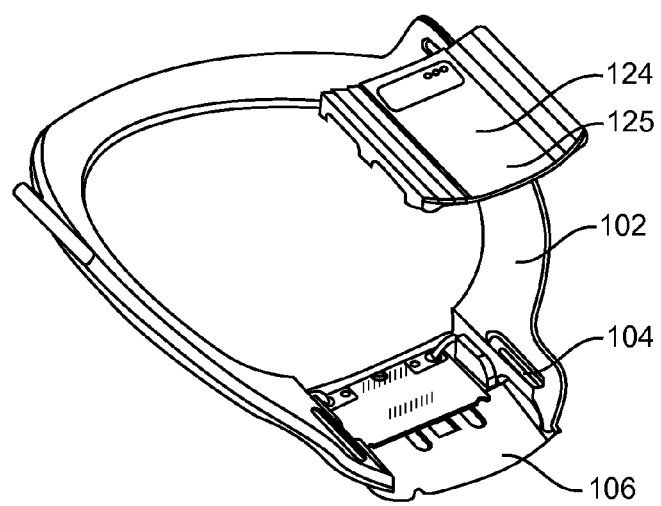
FIG. 22 illustrates a housing bottom of an electromagnetic treatment device.
Figure 23A:
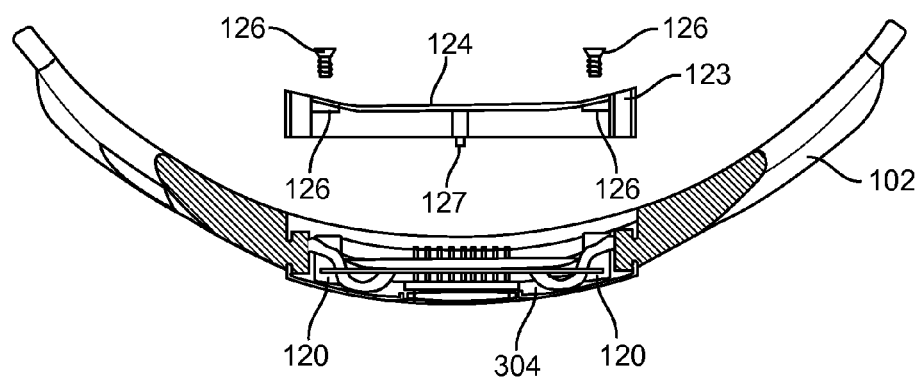
FIGS. 23A and 23B illustrate the attachment of the housing bottom to the stiffening member and housing top.
Figure 23B:
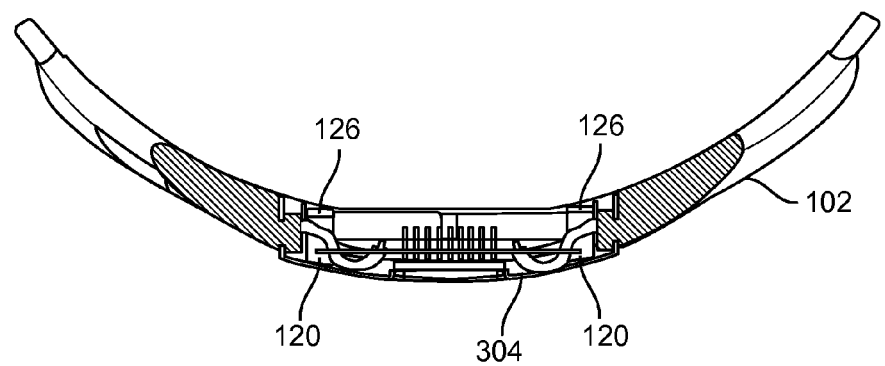
Figure 24:
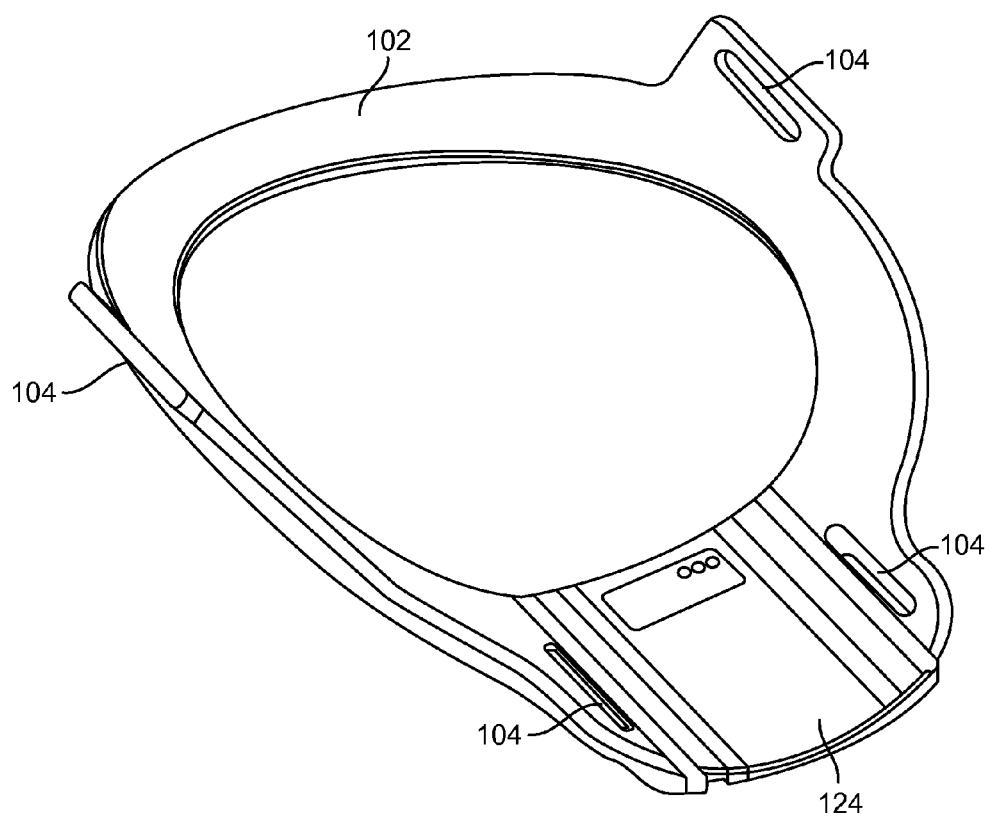
FIG. 24 shows the partially assembled electromagnetic treatment device with stiffening member, housing top, EMF applicator assembly, and housing bottom attached.

In further embodiments, the device 100 may include a housing bottom 124 designed to engage the housing top 106 and stiffening member 102 to provide a back cover to the housing top 106. FIGS. 22 and 23A-23B illustrate an embodiment of the treatment device 100 where the housing bottom 124 contains a back plate 125, a spacer 127, and attachment components 123, 126. The spacer 127 may be used to provide suitable space between the back plate 124 and the circuit board 304. The back plate 124 may also have attachment components 126 that engage with locking features 120 of the housing top 106. The attachment components may include components such as screws to attach the back plate 124 to the housing top 106. Additional attachment components such as mating grooves 123 may also be available to interface with the housing top 106 as needed. FIG. 24 shows the device 100 with the back plate 124 attached to the device 100.

Figure 25:
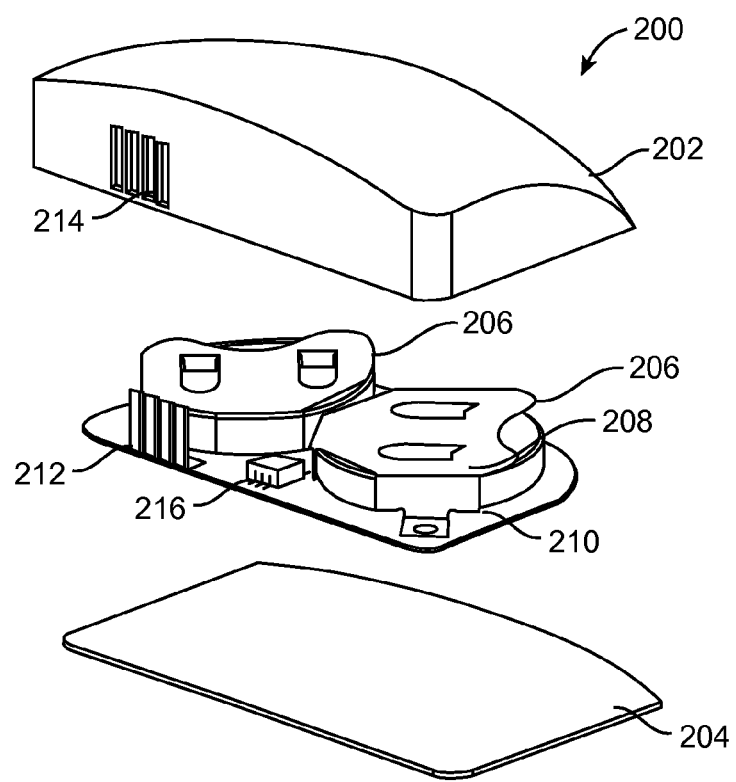
FIG. 25 illustrates an exploded view of a replaceable battery pack.
Figure 26:
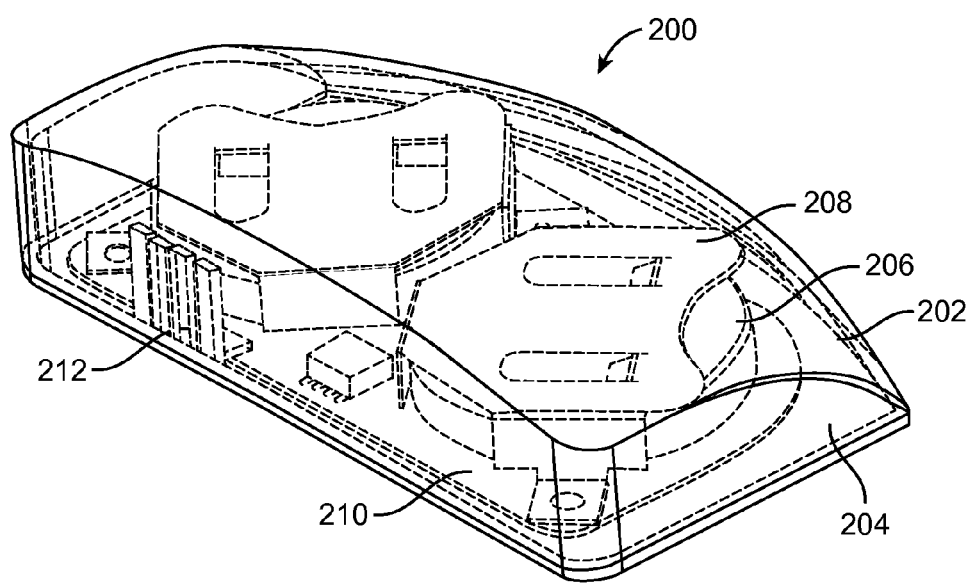
FIG. 26 shows an assembled battery pack.

In some embodiments, a removable power source is releasably connected to the device 100. FIGS. 25 and 26 provide an example of a replaceable battery pack 200 that can be used to provide power to the device 100. The replaceable battery pack 200 may include housing components such as a top housing 202 and a bottom housing 204. The housing can contain a circuit board 210 configured to couple to a battery or batteries 206. As shown in FIG. 25, the batteries 206 mounted onto the circuit board 210 are two CR2032 coil cell batteries. However, any variety or type of batteries may be used as needed. Additionally, the power source may provide power for a range of duration. In some cases, a disposable unit may only need power for a span of days. In such cases, the power source may not be replaceable and is integrated with the control circuit of the device 100. In other embodiments, the device 100 may need to run for longer and a replaceable power source separate from the control circuit of the device 100 allows for replacement of a depleted power source and continued use of the device. The replaceable power source may be a packet of battery packs for substitution into the device 100 once the attached pack is depleted. Alternatively, the replaceable power source may be a rechargeable battery pack that detaches from the device 100 to charge when not in use. The type of power supply source can be selected based on the desired treatment. For example, in some cases, running the device 100 for about 20 days to deliver treatment every fifteen minutes every hour and forty-five minutes may require a power supply that provides an output of 6 volt DC and 620 mA current capacity (which can be provided by two CR2032 cell batteries).

Additionally, a battery pack 200 may include an electrical interface 212 for connection to the control circuit or circuit board 304 of the EMF applicator assembly. The battery pack may further include an opening 214 to allow electrical connection between the electrical interface 212 and a connection component 109 of the circuit board 304. To attach the power source to the device 100, the device 100 may have a receiving portion 108 such as on the housing top 106 designed to releasably engage the battery pack housing.

In further embodiments, the battery pack can include a memory chip 216 that can store battery use data. The memory chip 216 may also include identifying information to prevent after-market sale of battery packs. The memory chip can also be configured to store treatment information such as treatment regimens that will be or have been provided by the device 100. A maximum limit for the number of treatments a battery pack can provide can also be stored on the memory chip 216.

Figure 27:
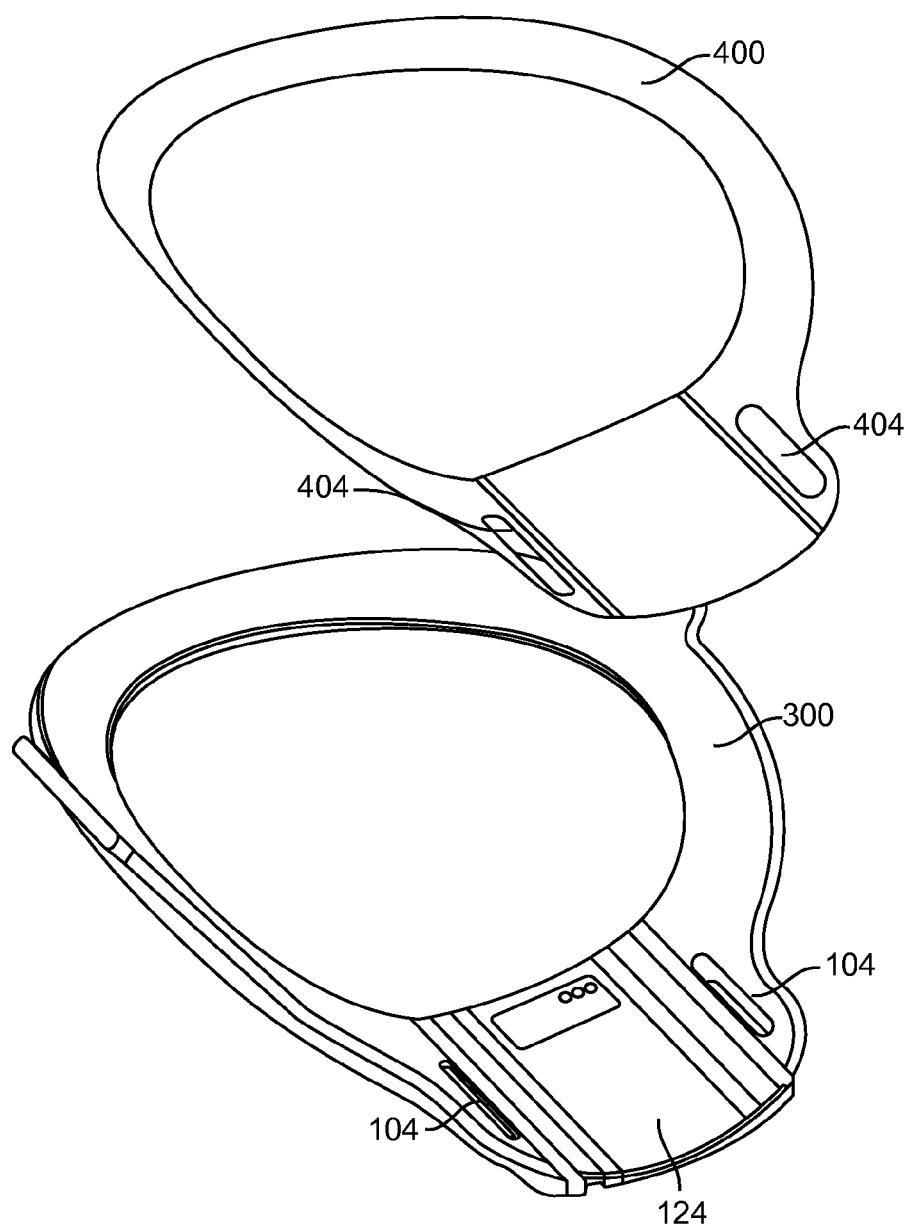
FIG. 27 illustrates a bottom cover for an electromagnetic treatment device.
Figure 28:
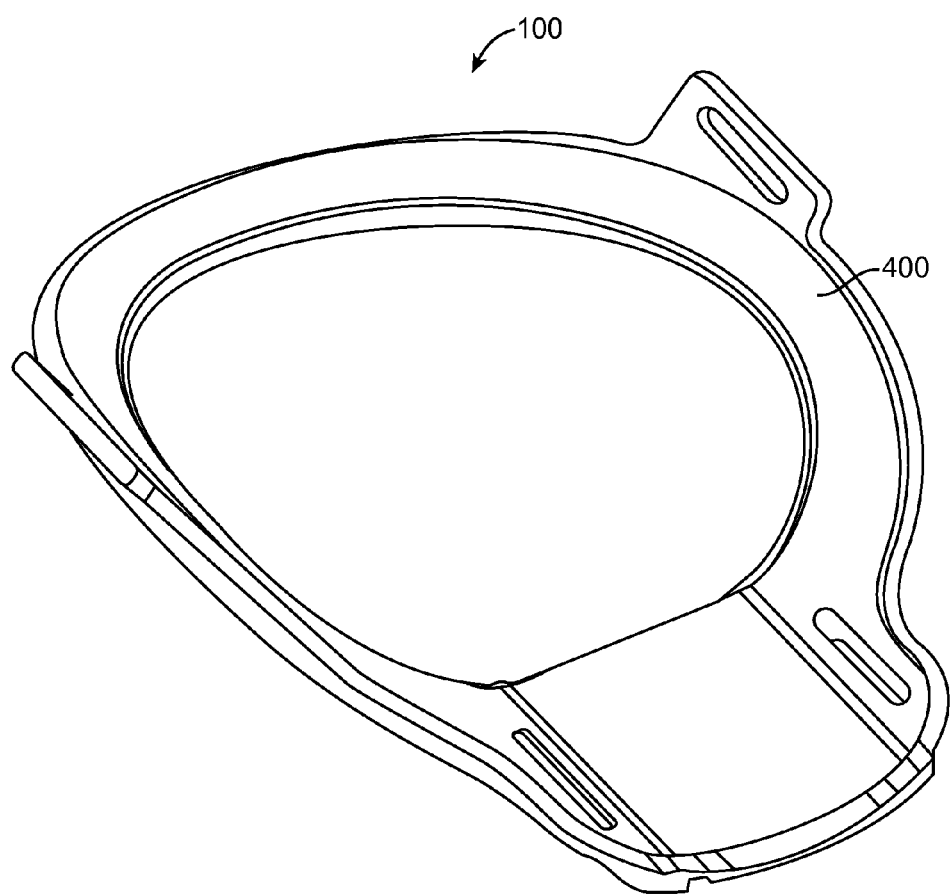
FIG. 28 illustrates a bottom cover attached to an electromagnetic delivery device.

In additional embodiments, the device 100 includes a bottom cover 400, shown in FIGS. 27 and 28, to be placed against the bottom surface of the device. The bottom cover 400 can cover the EMF applicator assembly 300 and the back plate 124. In embodiments where the applicator coil 102 rests in the groove 122, the bottom cover 400 can be used to further secure and protect the applicator coil 102 from deformation and breakage.

The device 100 may also include strap attaching elements 104 that allow for the device 100 to be adjustably worn by the subject. FIG. 27 shows the strap attaching elements 104 as eyelets through which wearable straps can be inserted and attached to the device. In some variations, the bottom cover 400 may also include strap attaching elements that may overlap with existing eyelets on the stiffening member. Although shown as an eyelet configured for insertion of a strap, the strap attaching element 104 can be any number or combination of attaching elements known in the art. For example, the straps may be attached to the device by use of a mated attachment mechanisms such as male and female buttons or clips or hook and loop.

Figure 29:
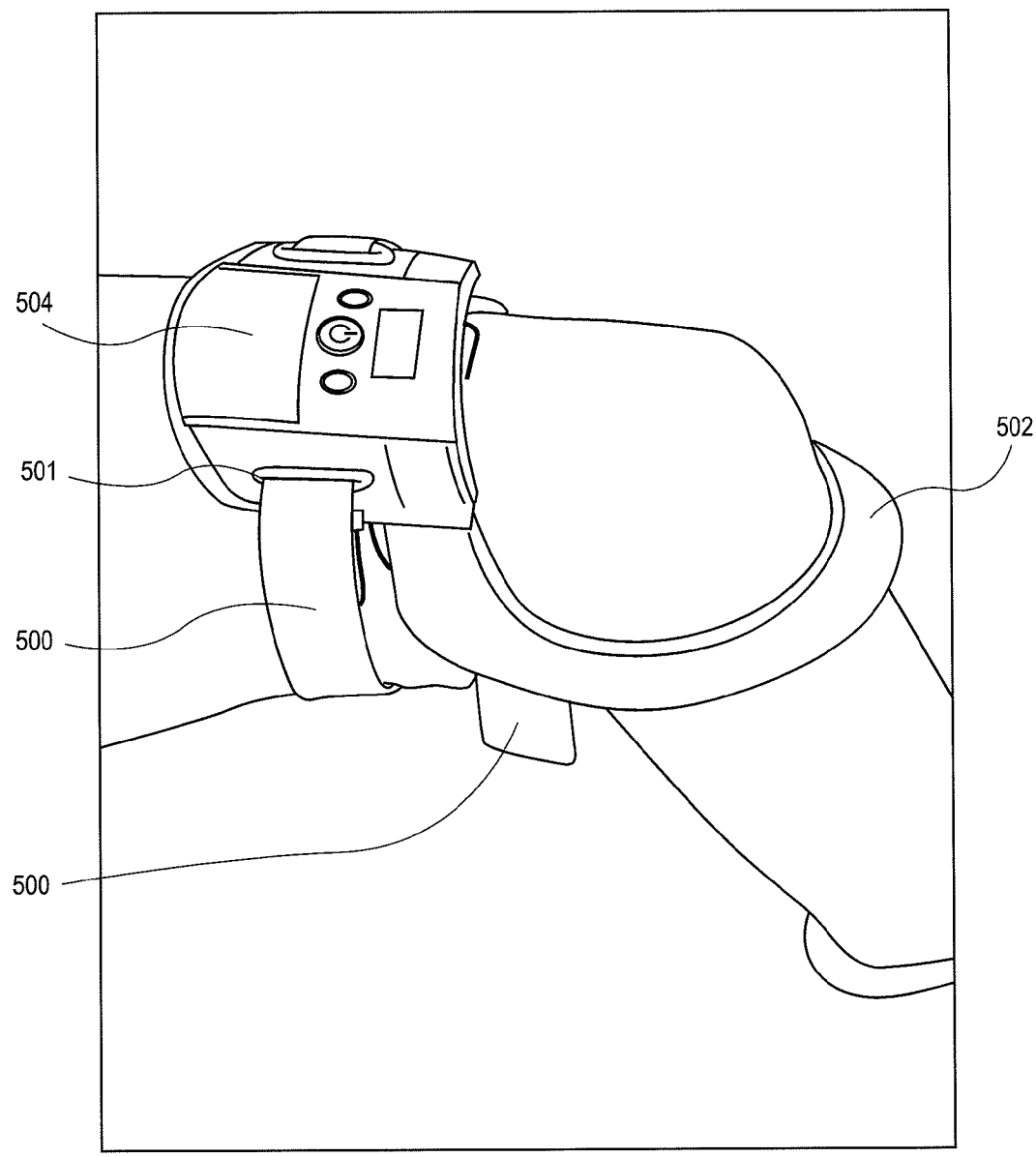
FIG. 29 illustrates an electromagnetic treatment device with adjustable straps worn around a knee.
Figure 30:
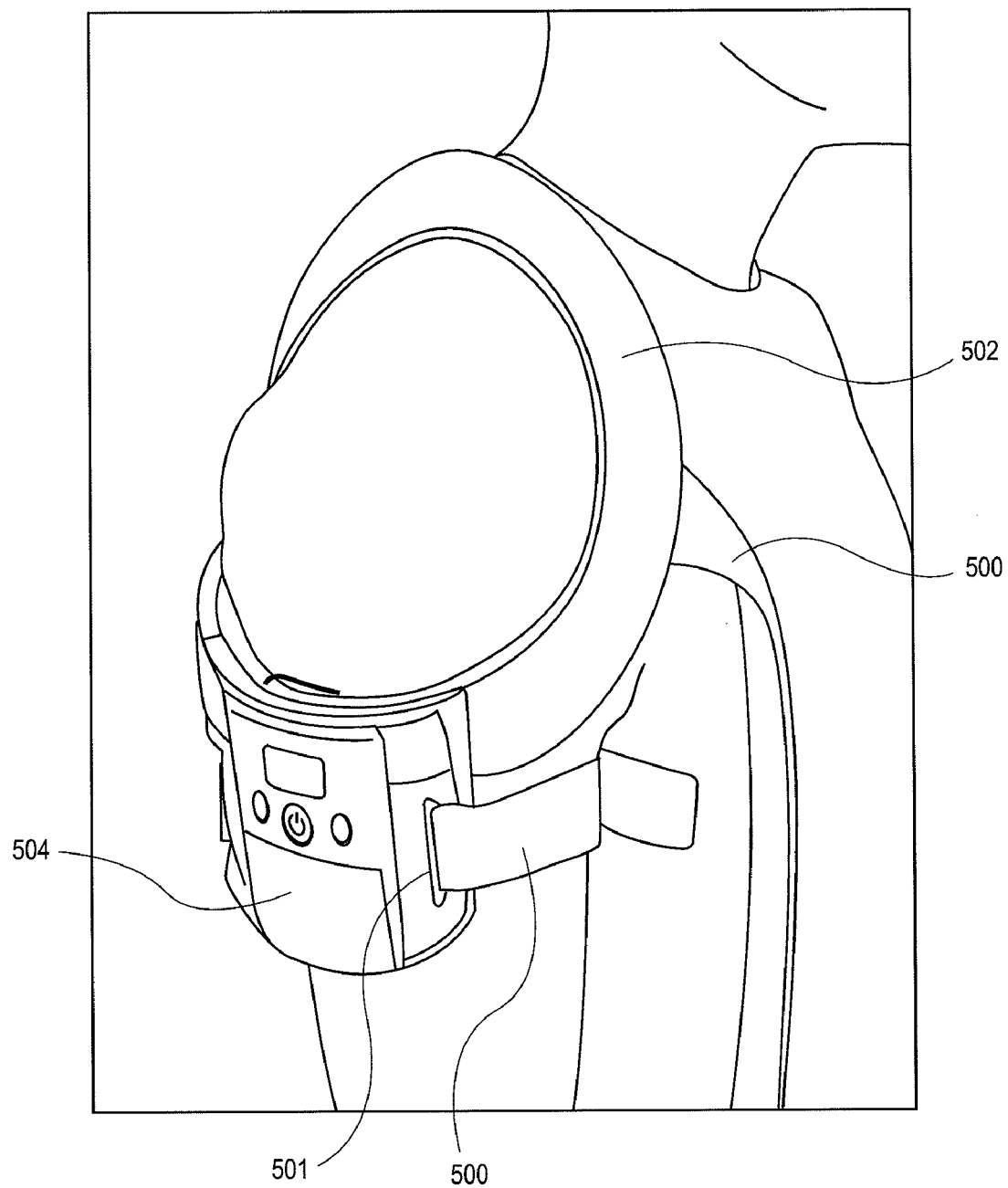
FIG. 30 illustrates an electromagnetic treatment device with adjustable straps worn around a shoulder.
Figure 31:
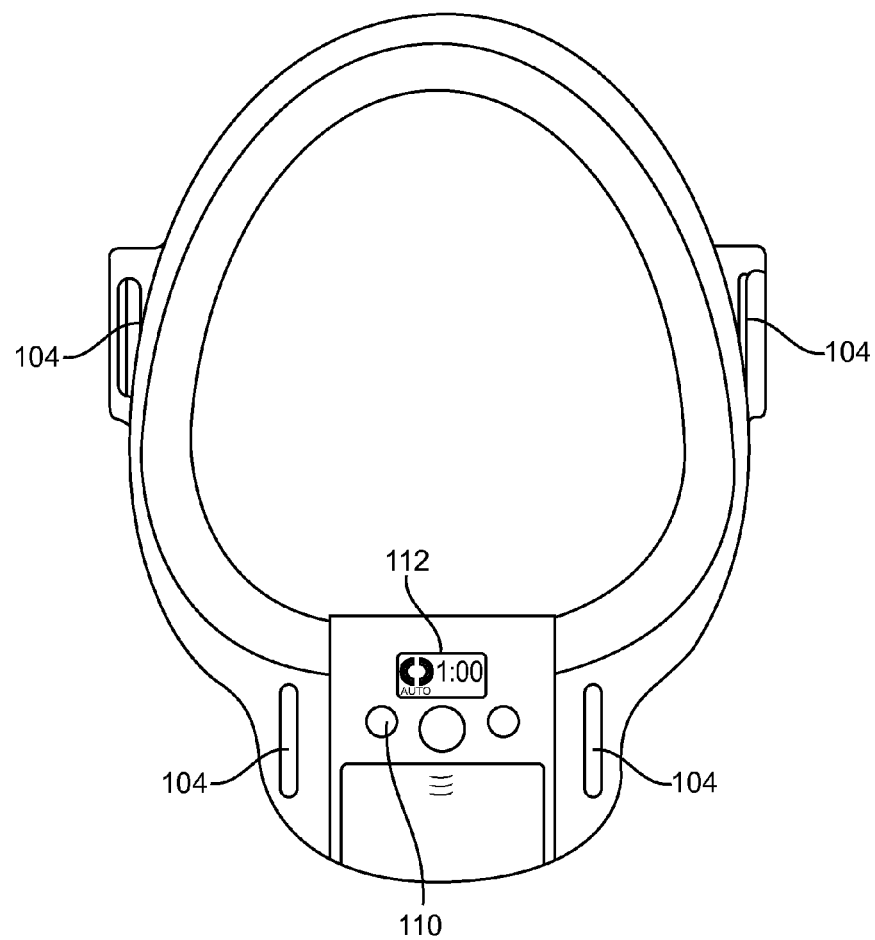
FIG. 31 illustrates an electromagnetic treatment device with a user interface.

FIG. 29 provides an example of the device 100 with adjustable straps 500 attached to device 504. Device 504 has a stiffening member 502 containing the applicator loop. The device 504 also includes eyelets 501 to accommodate adjustable straps 500. Additionally, the straps are designed to adjustably secure the device 504 to a leg portion of the subject such that the applicator loop surrounds the knee. Alternatively, the device 504 can be worn on the shoulder, shown in FIG. 30. The device 504 is worn on the upper arm of the subject with the stiffening member 502 surrounding the shoulder. The straps 500 are attached to eyelets 501 of the device 500 such that the subject can adjustably wear the device 504.

In additional embodiments, the device 100 can include user interface programming to provide subjects with treatment options and information about the device 100. For example, the device 100 may include a display screen 112 and input buttons 110. The device 100 may be programmed to notify the user on device information such as whether the device is active, duration of a treatment period, the time remaining for a treatment period, the duration of an inter-treatment period (a non-treatment period between treatment periods), remaining battery life, and whether the device is in automatic or manual operation mode. In further variations, the user interface provides audio indications of device or treatment information. For example, the device 100 may use sound alerts to inform the user that the device is active.

In further embodiments, the device 100 may be configured to operate in an automatic or manual mode. In the automatic mode, the device can provide pre-programmed treatment to the user. In the manual mode, the user can activate the device for a desired period of time or select between pre-programmed treatment options. Moreover, the device 100 may include a memory storage component to store the user's treatment data. This data may be stored on the device directly or communicated to another device such as computer, smart phone, printer, or other medical equipment/device.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. An electromagnetic treatment device for treating living tissue, wherein the device is compatible with a metal-containing implant or prosthesis, the device comprising:
    a control circuit configured to generate an electromagnetic signal;
    an applicator configured to deliver a calibrated time-varying magnetic field, the applicator calibrated to have substantially no inductive reactance and substantially no capacitance reactance when delivering the magnetic field in proximity to the metal-containing implant or prosthesis; and
    a tuning circuit comprising a resistor and an adjustable capacitor, wherein the tuning circuit is configured to calibrate the applicator to substantially eliminate an inductive component of reactance and a capacitive component of reactance of the applicator.

2. The control circuit of claim 1, wherein the control circuit is configured to provide an electromagnetic signal to the applicator to induce an electric field of peak amplitude between about 1 μV/m and about 100 V/m in the target tissue and a peak induced magnetic field between about 1 μT and about 0.1 T, wherein the signal generated by the control circuit comprises a burst of waveforms having a burst duration of greater than 50 μsec and a burst repetition rate of about 0.01 to about 1000 bursts per second.

3. The electromagnetic treatment device of claim 1, wherein the tuning circuit comprises an impedance value of about 50 ohms at 27.120 MHz.

4. The electromagnetic treatment device of claim 1, wherein the tuning circuit is coupled to the applicator and comprises, a resistor, an adjustable series capacitor, and an adjustable parallel capacitor.

5. The electromagnetic treatment device of claim 1, wherein the applicator comprises a loop applicator.

6. An electromagnetic treatment device comprising:
    a control circuit configured to generate an electromagnetic signal;
    an applicator configured to generate a calibrated electromagnetic field; and
    a tuning circuit connected to the applicator, wherein the tuning circuit is configured to substantially eliminate an inductive component of reactance and a capacitance component of reactance of the applicator when the applicator is positioned near a metal-containing implant
    wherein the tuning circuit comprises a resistor, an adjustable series capacitor, and an adjustable parallel capacitor.

7. The electromagnetic treatment device of claim 6, wherein the series capacitor and the parallel capacitor are configured to adjust the reactance of the applicator such that the reactance of the applicator is substantially purely resistive.

8. An electromagnetic treatment device comprising:
    an electromagnetic treatment device configured to provide an electromagnetic field to a target treatment location containing a metal-containing implant or prosthesis, the electromagnetic treatment device having an applicator and an adjustable circuit configured to correct electromagnetic interference caused by the metal-containing implant or prosthesis by reducing or eliminating an inductive component and a capacitance component of the applicator's reactance when the applicator is in proximity to the metal-containing implant or prosthesis, wherein the circuit further comprises an adjustable series capacitance and an adjustable parallel capacitance connected to the applicator.

9. The electromagnetic treatment device of claim 8, wherein the reactance is substantially purely resistive.

10. The electromagnetic treatment device of claim 8 further comprising a stiffening member configured to maintain the shape of the applicator.

11. The electromagnetic treatment device of claim 8 wherein the applicator comprises an applicator loop comprising a flexible metal coil.

* * * * *